United States Patent
Jordan et al.

(10) Patent No.: US 12,097,188 B2
(45) Date of Patent: *Sep. 24, 2024

(54) COMPOSITIONS AND METHODS FOR THE TREATMENT OF MACULAR DEGENERATION

(71) Applicant: Aldeyra Therapeutics, Inc., Lexington, MA (US)

(72) Inventors: Thomas A. Jordan, Lexington, MA (US); John Clifford Chabala, Scotch Plains, NJ (US); Gerald D. Cagle, Fort Worth, TX (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/241,598

(22) Filed: Sep. 1, 2023

(65) Prior Publication Data
US 2024/0148700 A1 May 9, 2024

Related U.S. Application Data

(63) Continuation of application No. 15/782,470, filed on Oct. 12, 2017, now abandoned, which is a continuation of application No. 13/514,769, filed as application No. PCT/US2010/059719 on Dec. 9, 2010, now Pat. No. 9,814,701.

(60) Provisional application No. 61/285,745, filed on Dec. 11, 2009.

(51) Int. Cl.
| A61K 31/423 | (2006.01) |
| A61K 9/00 | (2006.01) |
| A61K 31/47 | (2006.01) |
| A61K 47/40 | (2006.01) |

(52) U.S. Cl.
CPC .......... *A61K 31/423* (2013.01); *A61K 9/0048* (2013.01); *A61K 31/47* (2013.01); *A61K 47/40* (2013.01)

(58) Field of Classification Search
CPC ....... A61K 31/47; A61K 47/40; A61K 9/0048
See application file for complete search history.

(56) References Cited

U.S. PATENT DOCUMENTS

| 2,086,186 A | 7/1937 | Messer |
| 3,912,748 A | 10/1975 | Evans et al. |
| 4,668,626 A | 5/1987 | Kobayashi et al. |
| 4,956,351 A | 9/1990 | Mesens et al. |
| 5,024,998 A | 6/1991 | Bodor |
| 5,032,392 A | 7/1991 | Varma |
| 5,364,637 A | 11/1994 | De et al. |
| 5,376,645 A | 12/1994 | Stella et al. |
| 5,419,898 A | 5/1995 | Ikejiri et al. |
| 5,472,954 A | 12/1995 | Loftsson |
| 5,493,027 A | 2/1996 | Nichols et al. |
| 5,576,311 A | 11/1996 | Guy |
| 5,668,117 A | 9/1997 | Shapiro |
| 5,767,109 A | 6/1998 | Sanchez et al. |
| 5,998,488 A | 12/1999 | Shinohara et al. |
| 6,107,300 A | 8/2000 | Bakthavatchalam et al. |
| 6,191,127 B1 | 2/2001 | Holscher et al. |
| 6,358,948 B1 | 3/2002 | Zhang et al. |
| 6,444,221 B1 | 9/2002 | Shapiro |
| 6,492,520 B1 | 12/2002 | Chen |
| 6,498,154 B1 | 12/2002 | Grubb et al. |
| 6,515,010 B1 | 2/2003 | Franchini et al. |
| 6,525,056 B2 | 2/2003 | Arvanitis et al. |
| 6,569,879 B2 | 5/2003 | Liu et al. |
| 7,083,803 B2 | 8/2006 | Peyman |
| 7,297,709 B2 | 11/2007 | Dai et al. |
| 7,531,564 B2 | 5/2009 | Malamas et al. |
| 7,563,906 B2 | 7/2009 | Hagihara et al. |
| 7,842,312 B2 | 11/2010 | Burgermeister et al. |
| 7,956,189 B2 | 6/2011 | Chen et al. |
| 7,973,025 B2 | 7/2011 | Jordan et al. |
| 7,982,071 B2 | 7/2011 | Scott et al. |
| 8,158,609 B1 | 4/2012 | Marsh et al. |
| 8,435,965 B2 | 5/2013 | Tabuchi et al. |
| 8,490,764 B2 | 7/2013 | Simester |
| 8,575,221 B2 | 11/2013 | Masse et al. |
| 8,722,669 B2 | 5/2014 | Palczewski et al. |
| 8,791,154 B2 | 7/2014 | Gamache et al. |
| 8,940,721 B2 | 1/2015 | Jordan et al. |

(Continued)

FOREIGN PATENT DOCUMENTS

| CA | 3032609 A1 | 3/2018 |
| CN | 1830964 A | 9/2006 |

(Continued)

OTHER PUBLICATIONS

"Shin iyakuhin no kikaku oyobi shaken houhou no settei nituite nituite (Regarding the setting of the standard and test method of a new medical product" PMSB/ELD Notification No. 568, May 2001, 46 pages (Only Official copy).

Aldeyra Therapeutics, "Positive Results from Phase IIa Clinical Trials in Subjects with Allergic Conjunctivitis", Press Release, Feb. 29, 2016, 3 pages.

Caira, "Crystalline Polymorphism of Organic Compounds", Topics in Current Chemistry, Jan. 1999, 198:163-208.

Kawaguchi et al., "Drug and crystal polymorphism," Journal of human environmental engineering, 2002, 4(2):310-317.

Maghsoodi et al., "Physicomechanical Properties of Naproxen-Loaded Microparticles Prepared from Eudragit L100", AAPS PharmSciTech., Mar. 2009, 10(1):120-128.

(Continued)

*Primary Examiner* — James D. Anderson
(74) *Attorney, Agent, or Firm* — Dechert LLP; Andrea L. C. Reid; Joseph W. Arico

(57) ABSTRACT

The present invention is directed to topical ophthalmic compositions of a lipophilic compound and an oligomeric or polymeric carrier wherein the compositions are useful in the treatment and prevention of macular degeneration. The invention also includes methods of treating macular degeneration by using a topical ophthalmic composition of a lipophilic compound and an oligomeric or polymeric carrier.

19 Claims, 3 Drawing Sheets

(56) References Cited

U.S. PATENT DOCUMENTS

| | | |
|---|---|---|
| 8,940,764 B2 | 1/2015 | Jordan et al. |
| 9,067,963 B2 | 6/2015 | Thompson et al. |
| 9,084,730 B2 | 7/2015 | Bedos et al. |
| 9,259,427 B2 | 2/2016 | Tierney et al. |
| 9,265,759 B2 | 2/2016 | Jordan et al. |
| 9,364,430 B2 | 6/2016 | Babul |
| 9,364,471 B2 | 6/2016 | Jordan et al. |
| 9,375,408 B2 | 6/2016 | Singh |
| 9,562,039 B2 | 2/2017 | Julia Jane et al. |
| 9,604,997 B2 | 3/2017 | Jordan et al. |
| 9,650,342 B2 | 5/2017 | Jordan et al. |
| 9,663,526 B2 | 5/2017 | Fensome et al. |
| 9,687,481 B2 | 6/2017 | Brady et al. |
| 9,814,701 B2 | 11/2017 | Jordan et al. |
| 9,817,701 B2 | 11/2017 | Baptist et al. |
| 9,896,419 B2 | 2/2018 | Jordan et al. |
| 10,058,095 B2 | 8/2018 | Czarnik |
| 10,098,894 B2 | 10/2018 | Amadio et al. |
| 10,111,862 B2 | 10/2018 | Chabala et al. |
| 10,202,348 B2 | 2/2019 | Jordan et al. |
| 10,213,395 B2 | 2/2019 | Brady et al. |
| 10,414,732 B2 | 9/2019 | Buist et al. |
| 10,426,790 B2 | 10/2019 | Young et al. |
| 10,463,687 B2 | 11/2019 | Rodriguez-Boulan et al. |
| 10,543,181 B2 | 1/2020 | Brady et al. |
| 10,550,085 B2 | 2/2020 | Brady et al. |
| 10,588,874 B2 | 3/2020 | Brady et al. |
| 10,736,842 B2 | 8/2020 | Misra |
| 10,744,144 B2 | 8/2020 | Shah |
| 10,781,158 B2 | 9/2020 | Singh |
| 10,864,166 B2 | 12/2020 | Venkatesh et al. |
| 10,913,722 B2 | 2/2021 | Jordan et al. |
| 11,007,157 B2 | 5/2021 | Brady et al. |
| 11,040,039 B2 | 6/2021 | Macdonald et al. |
| 11,046,650 B2 | 6/2021 | Brady et al. |
| 11,129,823 B2 | 9/2021 | Brady et al. |
| 11,197,821 B2 | 12/2021 | Clark et al. |
| 11,312,692 B1 | 4/2022 | Machatha et al. |
| 11,459,300 B2 | 10/2022 | Brady et al. |
| 11,583,529 B2 | 2/2023 | Macdonald et al. |
| 11,701,331 B2 | 7/2023 | Brady et al. |
| 11,724,987 B2 | 8/2023 | Jordan et al. |
| 11,771,664 B2 | 10/2023 | Brady et al. |
| 11,786,518 B2 | 10/2023 | Clark et al. |
| 11,845,722 B2 | 12/2023 | Brady et al. |
| 2004/0132636 A1 | 7/2004 | Dooley et al. |
| 2004/0198828 A1 | 10/2004 | Abelson et al. |
| 2004/0235892 A1 | 11/2004 | Dai et al. |
| 2005/0020603 A1 | 1/2005 | Dai et al. |
| 2005/0090553 A1 | 4/2005 | Shapiro |
| 2005/0130906 A1 | 6/2005 | Matier et al. |
| 2005/0197292 A1 | 9/2005 | Smithson et al. |
| 2005/0234018 A1 | 10/2005 | Lyons et al. |
| 2006/0014786 A1 | 1/2006 | Raut |
| 2006/0111318 A1 | 5/2006 | Okamoto |
| 2006/0183909 A1 | 8/2006 | Schmitt et al. |
| 2006/0189608 A1 | 8/2006 | Bingaman |
| 2006/0257488 A1 | 11/2006 | Hubbard |
| 2007/0129404 A1 | 6/2007 | Hagihara et al. |
| 2007/0135481 A1 | 6/2007 | Jordan et al. |
| 2007/0243257 A1 | 10/2007 | Bedos et al. |
| 2007/0297981 A1 | 12/2007 | Ousler et al. |
| 2008/0108818 A1 | 5/2008 | Chen et al. |
| 2008/0241256 A1 | 10/2008 | Kuhn |
| 2009/0118503 A1 | 5/2009 | Sprott et al. |
| 2009/0182009 A1 | 7/2009 | Jordan et al. |
| 2010/0160304 A1 | 6/2010 | Katayama |
| 2010/0240624 A1 | 9/2010 | Chapin et al. |
| 2010/0331315 A1 | 12/2010 | Haddach et al. |
| 2011/0071091 A1 | 3/2011 | Chowhan et al. |
| 2011/0105450 A1 | 5/2011 | Chapin et al. |
| 2011/0257271 A1 | 10/2011 | Masse et al. |
| 2011/0263645 A1 | 10/2011 | Jordan et al. |
| 2012/0108585 A1 | 5/2012 | Vu |
| 2012/0295967 A1 | 11/2012 | Gamache et al. |
| 2012/0302601 A1 | 11/2012 | Jordan et al. |
| 2013/0165419 A1 | 6/2013 | Lindstrom et al. |
| 2013/0190500 A1 | 7/2013 | Greiner et al. |
| 2014/0038918 A1 | 2/2014 | Rodriguez-Boulan et al. |
| 2014/0050797 A1 | 2/2014 | Venkatesh et al. |
| 2014/0235604 A1 | 8/2014 | Palczewski et al. |
| 2014/0235722 A1 | 8/2014 | Jordine et al. |
| 2015/0209333 A1 | 7/2015 | Jordan et al. |
| 2015/0209345 A1 | 7/2015 | Jordan et al. |
| 2015/0258120 A1 | 9/2015 | Zarnitsyn et al. |
| 2015/0335632 A1 | 11/2015 | Brady et al. |
| 2015/0344432 A1 | 12/2015 | Jordan et al. |
| 2015/0344447 A1 | 12/2015 | Chabala et al. |
| 2016/0009698 A1 | 1/2016 | Julia Jane et al. |
| 2016/0030449 A1 | 2/2016 | Persicaner et al. |
| 2016/0052930 A1 | 2/2016 | Fensome et al. |
| 2016/0136231 A1 | 5/2016 | Gadek |
| 2016/0151381 A1 | 6/2016 | Blackburn et al. |
| 2016/0168098 A1 | 6/2016 | Jordan et al. |
| 2017/0029354 A1 | 2/2017 | Singh |
| 2017/0095449 A1 | 4/2017 | Winters et al. |
| 2017/0143627 A1 | 5/2017 | Misra |
| 2017/0239196 A1 | 8/2017 | Brady et al. |
| 2017/0266220 A1 | 9/2017 | Young et al. |
| 2017/0320829 A1 | 11/2017 | Jordan et al. |
| 2017/0354655 A1 | 12/2017 | Beaupre et al. |
| 2018/0050989 A1 | 2/2018 | Machatha et al. |
| 2018/0092882 A1 | 4/2018 | Jordan et al. |
| 2018/0194733 A1 | 7/2018 | Jordan et al. |
| 2018/0235980 A1 | 8/2018 | Shah |
| 2018/0250306 A1 | 9/2018 | Brady et al. |
| 2018/0265474 A1 | 9/2018 | Buist et al. |
| 2018/0354905 A1 | 12/2018 | Brady et al. |
| 2019/0054023 A1 | 2/2019 | Seaman et al. |
| 2019/0087646 A1 | 3/2019 | Goulden et al. |
| 2019/0105322 A1 | 4/2019 | Macdonald et al. |
| 2019/0125729 A1 | 5/2019 | Chabala et al. |
| 2019/0183878 A1 | 6/2019 | Brady et al. |
| 2019/0210971 A1 | 7/2019 | Aldeyra |
| 2019/0231715 A1 | 8/2019 | Brady et al. |
| 2019/0247334 A1 | 8/2019 | Brady et al. |
| 2020/0038392 A1 | 2/2020 | Brady et al. |
| 2020/0062712 A1 | 2/2020 | Machatha et al. |
| 2020/0121591 A1 | 4/2020 | Clark et al. |
| 2020/0199075 A1 | 6/2020 | Brady et al. |
| 2020/0246345 A1 | 8/2020 | Brady et al. |
| 2020/0323841 A1 | 10/2020 | Clark et al. |
| 2020/0368182 A1 | 11/2020 | Brady et al. |
| 2021/0269402 A1 | 9/2021 | Jordan et al. |
| 2021/0275469 A1 | 9/2021 | Brady et al. |
| 2021/0317385 A1 | 10/2021 | Macdonald et al. |
| 2021/0347735 A1 | 11/2021 | Brady et al. |
| 2021/0353628 A1 | 11/2021 | Macdonald et al. |
| 2021/0393527 A1 | 12/2021 | Brady et al. |
| 2021/0393612 A1 | 12/2021 | Machatha et al. |
| 2022/0017475 A1 | 1/2022 | Machatha et al. |
| 2022/0089542 A1 | 3/2022 | Machatha et al. |
| 2022/0133629 A1 | 5/2022 | Clark et al. |
| 2022/0133697 A1 | 5/2022 | Machatha et al. |
| 2022/0184057 A1 | 6/2022 | Brady et al. |
| 2022/0202745 A1 | 6/2022 | Brady et al. |
| 2022/0211691 A1 | 7/2022 | Brady et al. |
| 2022/0354857 A1 | 11/2022 | Brady et al. |
| 2023/0041335 A1 | 2/2023 | Jordan et al. |
| 2023/0131929 A1 | 4/2023 | Brady et al. |
| 2023/0149383 A1 | 5/2023 | Brady et al. |
| 2023/0174491 A1 | 6/2023 | Brady et al. |
| 2023/0228744 A1 | 7/2023 | Brady et al. |
| 2023/0248727 A1 | 8/2023 | Macdonald et al. |
| 2023/0293527 A1 | 9/2023 | Macdonald et al. |
| 2024/0132451 A1 | 4/2024 | Brady et al. |
| 2024/0139173 A1 | 5/2024 | Clark et al. |
| 2024/0174614 A1 | 5/2024 | Jordan et al. |

FOREIGN PATENT DOCUMENTS

| | | |
|---|---|---|
| CN | 1882339 A | 12/2006 |
| CN | 101048384 A | 10/2007 |
| CN | 101321742 A | 12/2008 |

(56) References Cited

FOREIGN PATENT DOCUMENTS

| | | |
|---|---|---|
| CN | 101534826 A | 9/2009 |
| CN | 101611009 A | 12/2009 |
| CN | 104884049 A | 9/2015 |
| CN | 105120866 A | 12/2015 |
| CN | 105704440 A | 6/2016 |
| CN | 108135867 A | 6/2018 |
| CN | 109640983 A | 4/2019 |
| CN | 111527530 A | 8/2020 |
| CN | 112541870 A | 3/2021 |
| CN | 112800947 A | 5/2021 |
| CN | 113168511 A | 7/2021 |
| EP | 0186367 A2 | 7/1986 |
| EP | 0245054 A1 | 11/1987 |
| EP | 0483881 A1 | 5/1992 |
| EP | 1621199 A1 | 2/2006 |
| EP | 1679308 A1 | 7/2006 |
| EP | 1888548 A1 | 2/2008 |
| EP | 2301549 A1 | 3/2011 |
| GB | 2327672 A | 2/1999 |
| JP | H04264422 A | 9/1992 |
| JP | H06239748 A | 8/1994 |
| JP | H07025758 A | 1/1995 |
| JP | H08175985 A | 7/1996 |
| JP | H09169647 A | 6/1997 |
| JP | H09285529 A | 11/1997 |
| JP | H10306022 A | 11/1998 |
| JP | 2001041757 A | 2/2001 |
| JP | 2001318350 A | 11/2001 |
| JP | 2002003364 A | 1/2002 |
| JP | 2003519698 A | 6/2003 |
| JP | 2005132834 A | 5/2005 |
| JP | 2005187407 A | 7/2005 |
| JP | 3736916 B2 | 1/2006 |
| JP | 2006008568 A | 1/2006 |
| JP | 2007532648 A | 11/2007 |
| JP | 2008542291 A | 11/2008 |
| JP | 4466875 B2 | 5/2010 |
| JP | 4748289 B2 | 8/2011 |
| JP | 2011203665 A | 10/2011 |
| JP | 2012506449 A | 3/2012 |
| JP | 5194218 B2 | 5/2013 |
| JP | 2014515355 A | 6/2014 |
| JP | 2015057437 A | 3/2015 |
| JP | 2015535293 A | 12/2015 |
| JP | 2016508994 A | 3/2016 |
| JP | 2018523700 A | 8/2018 |
| JP | 2018530524 A | 10/2018 |
| JP | 2019507756 A | 3/2019 |
| KR | 20180073554 A | 7/2018 |
| RU | 2010137842 A | 3/2012 |
| RU | 2565448 C2 | 10/2015 |
| SU | 50906 A1 | 11/1936 |
| SU | 509046 A1 | 6/1984 |
| WO | WO-199507274 A1 | 3/1995 |
| WO | WO-1996022992 A1 | 8/1996 |
| WO | WO-1998005645 A1 | 2/1998 |
| WO | WO-1999046237 A1 | 9/1999 |
| WO | WO-2001041757 A1 | 6/2001 |
| WO | WO-2001051919 A2 | 7/2001 |
| WO | WO-2004082622 A2 | 9/2004 |
| WO | WO-2004091630 A1 | 10/2004 |
| WO | WO-2005035506 A1 | 4/2005 |
| WO | WO-2005040151 A1 | 5/2005 |
| WO | WO-2005051328 A2 | 6/2005 |
| WO | WO-2005079774 A2 | 9/2005 |
| WO | WO-2005105067 A2 | 11/2005 |
| WO | WO-2006000421 A2 | 1/2006 |
| WO | WO-2006002473 A1 | 1/2006 |
| WO | WO-2006049968 A1 | 5/2006 |
| WO | WO-2006077821 A1 | 7/2006 |
| WO | WO-2006127945 A1 | 11/2006 |
| WO | WO-2007118276 A1 | 10/2007 |
| WO | WO-2008014602 A1 | 2/2008 |
| WO | WO2008052086 A1 | 5/2008 |
| WO | WO-2009045479 A1 | 4/2009 |
| WO | WO-2009102418 A1 | 8/2009 |
| WO | WO-2010048332 A2 | 4/2010 |
| WO | WO-2010133672 A1 | 11/2010 |
| WO | WO-2011008202 A1 | 1/2011 |
| WO | WO-2011071995 A2 | 6/2011 |
| WO | WO-2011072141 A1 | 6/2011 |
| WO | WO-2011078204 A1 | 6/2011 |
| WO | WO-2012097173 A2 | 7/2012 |
| WO | WO-2012105887 A1 | 8/2012 |
| WO | WO-2014100425 A1 | 6/2014 |
| WO | WO-2014116593 A1 | 7/2014 |
| WO | WO-2014116836 A2 | 7/2014 |
| WO | WO-2015002893 A1 | 1/2015 |
| WO | WO-2015187942 A1 | 12/2015 |
| WO | WO-2016085939 A2 | 6/2016 |
| WO | WO-2016165626 A1 | 10/2016 |
| WO | WO-2017035077 A1 | 3/2017 |
| WO | WO-2017035082 A1 | 3/2017 |
| WO | WO-2017147617 A1 | 8/2017 |
| WO | WO-2017196881 A1 | 11/2017 |
| WO | WO-2017214201 A1 | 12/2017 |
| WO | WO-2018039192 A1 | 3/2018 |
| WO | WO-2018039197 A1 | 3/2018 |
| WO | WO-2018064354 A1 | 4/2018 |
| WO | WO-2018067860 A1 | 4/2018 |
| WO | WO2018071619 A1 | 4/2018 |
| WO | WO2018091859 A1 | 5/2018 |
| WO | WO-2018170476 A1 | 9/2018 |
| WO | WO-2019075136 A1 | 4/2019 |
| WO | WO-2020018498 A1 | 1/2020 |
| WO | WO-2020028820 A1 | 2/2020 |
| WO | WO-2020033344 A1 | 2/2020 |
| WO | WO-2020068986 A1 | 4/2020 |
| WO | WO-2020072621 A1 | 4/2020 |
| WO | WO-2020118045 A1 | 6/2020 |
| WO | WO-2020198064 A1 | 10/2020 |
| WO | WO-2020223685 A1 | 11/2020 |
| WO | WO-2020223717 A1 | 11/2020 |
| WO | WO-2021051003 A1 | 3/2021 |
| WO | WO-2021195211 A1 | 9/2021 |
| WO | WO-2021211625 A1 | 10/2021 |
| WO | WO-2021231792 A1 | 11/2021 |
| WO | WO-2021248031 A1 | 12/2021 |
| WO | WO-2022150580 A1 | 7/2022 |
| WO | WO-2023278816 A1 | 1/2023 |

OTHER PUBLICATIONS

*Neptune Generics, LLC v. Auspex Pharmaceuticals, Inc.*, IPR2015-01313, Paper No. 25, Dec. 9, 2015, 23 pages.
Noriyuki Takada "Souyaku dankai ni okeru genyaku Form sukuri ningu to sentaku (Bulk drug screening and selection in a drug development phase," Pharm Stage, Jan. 2007, 6(10):20-25.
Ono, "Analysis of Salt Selection of Current Active Pharmaceutical Ingredients (API)," Journal of Pharmaceutical Science and Technology, 2013, 73(3):176-182.
Pearl et al, "Inherited disorders of gamma-aminobutyric acid metabolism and advances in ALDH5A1 mutation dentification," Dev Med Child Neurol., 2015, 57(7):611-617.
Peralta et al., "Distinct Primary Structures, Ligand-binding Properties and Tissue-Specific Expression of Four Human Muscarinic Acetylcholine Receptors," Embo. J., 1987, 6:3923-3929.
Pickering, "Pharmacological Characterization of Melatonin Binding Sites in Syrian Hamster Hypothalamus," Em. J. Pharmacol., 1990, 175:71-77.
Pubchem CID 149143404, Aug. 12, 2020, 2 pages.
Pubchem CID 4391047, Sep. 14, 2005, 2 pages.
Pufahl et al., "Development of a fluorescence-based enzyme assay of human 5-lipoxygenase," Anal. Biochem., 2007, 364:204-212.
Quinlan et al., "4-Hydroxy-2-Nonenal Levels Increase in the Plasma of Patients with Adult Respiratory Distress Syndrome as Linoleic Acid Appears to Fall," Free Radic Res. 1994, 21(2):95-106.
Radu et al., "Isotretinoin treatment inhibits lipofuscin accumulation in a mouse model of recessive Stargardt's macular degeneration, " Novartis Foundation Symposium, 2004, 255:51-63(Abstract Only).
Radu et al., "Treatment with isoretinin inhibits lipofusion accumulation in a mouse model of recessive Stargardt's macular degeneration," Proc Natl Acad Sci. USA, 2003, 100(8):4742-4747.

(56) References Cited

OTHER PUBLICATIONS

Rejewski et al., "Pharmaceutical applications of cyclodextrins. 2. In vivo drug delivery," J Pharm Sci, Nov. 1996, 85(11):1142-1169.
Rapp et al., "The effects of local anesthetics on retinal function," Vision Research, 1982, 22:1097-1103.
Rauli et al., "Validation of Malondialdehyde and 4-Hydroxy-2-trans-Nonenal Measurement in Plasma by NICI-GC-MSI," J Biochem, 1998, 123:918-923.
Reed, "Lipid peroxidation and neurodegenerative disease", Free Radical Biology and Medicine, 2011, 51(7):1302-1319.
Rees et al., "Cloning and characterisation of the human 5-HT5A serotonin receptor," FEBS Lett., 1994, 355:242-246.
Reproxalap (Medchem Express), 2013, 3 pages.
Reynolds et al., "(-)-[3H] desmethoxyverapamil labels multiple calcium. Channel modulator receptors in brain and skeletal muscle membranes: differentiation by temperature and dihydropyridines," J. Pharmacol. Exp. Ther., 1986, 237:731-738.
Ricca et al., "Amphetamine derivatives and obesity," Appetite, Apr. 2009, 52(2):405-409.
Rinaldi-Carmona et al., "Characterization of two cloned human CB1 cannabinoid receptor isoforms," J. Pharmacol. Exp. Ther., 1996, 278:871-878.
Rivkees et al., "Identification of domains of the human A 1 adenosine receptor that are important for binding receptor subtype-selective ligands using chimeric A 1 /A2a adenosine receptors," J. Biol. Chem., 270:20485-20490 (1995).
Rizzo et al., "Aldehyde Trapping Agent NS2 Blocks Formation of Fatty Aldehyde Adducts with Phosphatidylethanolamine and Suggests Potential Therapeutic Approach for Sjogren-Larsson Syndrome," Mol Genet and Metab, 114(3):362A (Mar. 2015) [Abstract Only].
Rizzo et al., "Endogenous antioxidants and radical scavengers," Advances in Experimental Medicine and Biology, 2010, 698:52-56.
Rizzo et al., "Ichthyosis in Sjogren-Larsson syndrome reflects defective barrier function due to abnormal lamellar body structure and secretion," Arch Dermatol Res, 2010, 302(6):443-451.
Rizzo et al., "Sjogren-Larsson syndrome: molecular genetics and biochemical pathogenesis of fatty aldehyde dehydrogenase deficiency," Mol Genet Metab., 2007, 90(1):1-9.
Rizzo, "Fatty aldehyde and fatty alcohol metabolism: review and importance for epidermal structure and function", Biochim Biophys Acta, 2014, 1841(3):377-389.
Rizzo, "Genetics and prospective therapeutic targets for Sjogren-Larsson Syndrome," Expert Opin Orphan Drugs. 2016, 4(4):395-406.
Rizzo, "The role of fatty aldehyde dehydrogenase in epidermal structure and function" Dermato-Endocrinol, 2011, 3(2):91-99.
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Keratoconjunctivitis Sicca," Merck Manual Professional Version, 5 pages (2016), Available at: https://www.merckmanuals.com/professional/eye-disorders/corneal-disorders/keratoconjunctivitis-sicca.
Roat, "Ocular Mucous Membrane Pemphigoid," Merck Manual Professional Version, 3 pages (2016), Available at: https://www.merckmanuals.com/professional/eye-disorders/conjunctival-and-scleral-disorders/ocular-mucous-membrane-pemphigoid.
Roat, "Scleritis," Merck Manual Professional Version, 3 pages (2016), Available at: https://www.merckmanuals.com/professional/eye-disorders/conjunctival-and-scleral-disorders/scleritis.
Roberts et al., "Basic Principles of Organic Chemistry," 2nd edition, copyright 1977 W. A. Benjamin, Inc., pp. 580-582.
Saal, et al. "Pharmaceutical salts: A summary on doses of salt formers from the Orange Book", European Journal of Pharmaceutical Sciences, Jul. 16, 2013, 49(4):614-623.
Serajuddin, "Salt formation to improve drug solubility," Adv Drug Deliv Rev. 2007, 59(7):603-616.
Smalley, Science of Synthesis, 2002, 11:289.

Tanna et al., "Stargardt disease: clinical features, molecular genetics, animal models and therapeutic options," Br J Ophthalmol. 2017; 101 (1):25-30.
Tripathi et al., "Monoamine oxidase-B inhibitors as potential neurotherapeutic agents: An overview and update", Med Res Rev. Sep. 2019, 39(5):1603-1706.
Wermuth, "The Practice of Medicinal Chemistry," Elsevier, Second vol. 1999, pp. 347-365.
Yamano, "Approach to Crystal Polymorph in Process Research of New Drug," Journal of Synthetic Organic Chemistry, 2007, 65:907-913.
Yoko et al., "Drug and Crystal Polymorphism", Journal of Human Environmental Engineering, 2002, 4(2):310-317.
Young et al., "NS2, a novel aldehyde trap, decreases aldehyde levels in dry skin and eye models," Aldeyra therapeutics, 2014, 1 page.
Extended European Search Report received for European Patent Application No. 13865015.5 dated Mar. 31, 2016, 9 pages.
Extended European Search Report received for European Patent Application No. 19891719.7 dated Jul. 27, 2022, 9 pages.
Partial Supplementary European Search Report received for European Patent Application No. 14743711.5 dated Jul. 20, 2016, 14 pages.
PCT International Preliminary Report on Patentability received for PCT/US2006/020320, dated Nov. 30, 2007, 8 pages.
PCT International Preliminary Report on Patentability received for PCT/US2010/059719, dated Jun. 21, 2012, 7 pages.
PCT International Preliminary Report on Patentability received for PCT/US2013/076592, dated Jul. 2, 2015, 7 pages.
PCT International Preliminary Report on Patentability received for PCT/US2014/012356, dated Aug. 6, 2015, 8 pages.
PCT International Preliminary Report on Patentability received for PCT/US2014/012762, dated Aug. 6, 2015, 9 pages.
PCT International Preliminary Report on Patentability received for PCT/US2016/048054, dated Mar. 8, 2018, 6 pages.
PCT International Preliminary Report on Patentability received for PCT/US2016/048064, dated Mar. 8, 2018, 7 pages.
PCT International Preliminary Report on Patentability received for PCT/US2017/020020, dated Sep. 7, 2018, 10 pages.
PCT International Preliminary Report on Patentability received for PCT/US2017/047945, dated Mar. 7, 2019, 7 pages.
PCT International Preliminary Report on Patentability received for PCT/US2017/047958, dated Mar. 7, 2019, 08 pages.
PCT International Preliminary Report on Patentability received for PCT/US2018/023000, dated Sep. 26, 2019, 7 pages.
PCT International Preliminary Report on Patentability received for PCT/US2018/055310, dated Apr. 23, 2020, 6 pages.
PCT International Preliminary Report on Patentability received for PCT/US2019/052961, dated Apr. 8, 2021, 9 pages.
PCT International Preliminary Report on Patentability received for PCT/US2019/054263, dated Apr. 15, 2021, 11 pages.
PCT International Preliminary Report on Patentability received for PCT/US2019/064669, dated Jun. 17, 2021, 10 pages.
PCT International Preliminary Report on Patentability received for PCT/US2020/024022, dated Oct. 7, 2021, 9 pages.
PCT International Preliminary Report on Patentability received for PCT/US2020/031138, dated Nov. 11, 2021, 6 pages.
PCT International Preliminary Report on Patentability received for PCT/US2020/031219, dated Nov. 11, 2021, 11 pages.
PCT International Preliminary Report on Patentability received for PCT/US2021/023884, dated Oct. 6, 2022, 8 pages.
PCT International Preliminary Report on Patentability received for PCT/US2021/027148, dated Oct. 27, 2022, 7 pages.
PCT International Preliminary Report on Patentability received for PCT/US2021/032335, dated Nov. 24, 2022, 9 pages.
PCT International Preliminary Report on Patentability received for PCT/US2021/035948, dated Dec. 15, 2022, 8 pages.
PCT International Search Report and Written Opinion received for PCT/CN2022/113284, dated Nov. 2, 2022, 6 pages.
PCT International Search Report and Written Opinion received for PCT/US2006/020320, dated Sep. 26, 2006, 10 pages.
PCT International Search Report and Written Opinion received for PCT/US2010/059719, dated Feb. 8, 2011, 8 pages.

(56) References Cited

OTHER PUBLICATIONS

PCT International Search Report and Written Opinion received for PCT/US2013/076592, dated Apr. 30, 2014, 10 pages.
PCT International Search Report and Written Opinion received for PCT/US2014/012356, dated May 30, 2014, 11 pages.
PCT International Search Report and Written Opinion received for PCT/US2014/012762, dated Jul. 18, 2014, 12 pages.
PCT International Search Report and Written Opinion received for PCT/US2016/040064, dated Sep. 2, 2016, 8 pages.
PCT International Search Report and Written Opinion received for PCT/US2016/048054, dated Nov. 4, 2016, 8 pages.
PCT International Search Report and Written Opinion received for PCT/US2016/048064, dated Nov. 15, 2016, 8 pages.
PCT International Search Report and Written Opinion received for PCT/US2017/020020, dated May 24, 2017, 12 pages.
PCT International Search Report and Written Opinion received for PCT/US2017/031808, dated Aug. 11, 2017, 10 pages.
PCT International Search Report and Written Opinion received for PCT/US2017/047945, dated Oct. 20, 2017, 9 pages.
PCT International Search Report and Written Opinion received for PCT/US2017/047958, mailed on Oct. 31, 2017, 10 pages.
PCT International Search Report and Written Opinion received for PCT/US2018/023000, dated Jun. 1, 2018, 8 pages.
PCT International Search Report and Written Opinion received for PCT/US2018/055310, dated Jan. 29, 2019, 9 pages.
PCT International Search Report and Written Opinion received for PCT/US2019/041942, dated Sep. 30, 2019, 18 pages.
PCT International Search Report and Written Opinion received for PCT/US2019/044929, dated Nov. 20, 2019, 15 pages.
PCT International Search Report and Written Opinion received for PCT/US2019/045206, dated Oct. 17, 2019, 13 pages.
PCT International Search Report and Written Opinion received for PCT/US2019/052961, dated Dec. 10, 2019, 11 pages.
PCT International Search Report and Written Opinion received for PCT/US2019/054263, dated Jan. 6, 2020, 13 pages.
PCT International Search Report and Written Opinion received for PCT/US2019/064669, dated Feb. 27, 2020, 12 pages.
PCT International Search Report and Written Opinion received for PCT/US2019/069097 dated Apr. 30, 2020, 9 pages.
PCT International Search Report and Written Opinion received for PCT/US2020/024022, dated Jun. 17, 2020, 11 pages.
PCT International Search Report and Written Opinion received for PCT/US2020/031138, dated Jul. 13, 2020, 7 pages.
PCT International Search Report and Written Opinion received for PCT/US2020/031219, dated Aug. 31, 2020, 14 pages.
PCT International Search Report and Written Opinion received for PCT/US2020/050565, dated Dec. 22, 2020, 9 pages.
PCT International Search Report and Written Opinion received for PCT/US2021/023884, dated Jul. 28, 2021, 11 pages.
PCT International Search Report and Written Opinion received for PCT/US2021/027148, dated Jun. 28, 2021, 9 pages.
PCT International Search Report and Written Opinion received for PCT/US2021/032335, dated Jul. 27, 2021, 11 pages.
PCT International Search Report and Written Opinion received for PCT/US2021/035948, dated Oct. 26, 2021, 12 pages.
PCT International Search Report and Written Opinion received for PCT/US2022/011604, dated Mar. 25, 2022, 12 pages.
PCT International Search Report and Written Opinion received for PCT/US2022/035898, dated Nov. 16, 2022, 13 pages.
Search Report and Written Opinion received by the Intellectual Property Office of Singapore for Singapore Patent Application No. 11201505587Y, dated Jul. 12, 2016 (12 pages).
Search Report and Written Opinion received by the Intellectual Property Office of Singapore for Singapore Patent Application No. 11201505599Y dated Sep. 14, 2016 (5 pages).
U.S. Appl. No. 15/437,699 of Jordan et al., filed Feb. 21, 2017.
U.S. Appl. No. 17/305,915 of Machatha et al., filed Jul. 16, 2021.
U.S. Appl. No. 16/547,930 of Buist et al., filed Aug. 22, 2019.

Abelson and Loeffler, "Conjunctival allergen challenge: models in the investigation of ocular allergy," Curr Allergy Asthma Rep. 2003;3(4):363-8.
Abelson and Spitalny, "Combined analysis of two studies using the conjunctival allergen challenge model to evaluate olopatadine hydrochloride, a new ophthalmic antiallergic agent with dual activity," Am J Ophthalmol. 1998;125(6):797-804.
Abelson et al., "Conjunctival allergen challenge. A clinical approach to studying allergic conjunctivitis," Arch Ophthalmol. 1990;108(1):84-8.
Abelson et al., "The conjunctival provocation test model of ocular allergy: utility for assessment of an ocular corticosteroid, loteprednol etabonate," J Ocul Pharmacol Ther. 1998;14(6):533-42.
Abramovitz et al., "The utilization of recombinant prostanoid receptors to determine the affinities and selectivities of prostaglandins and related analogs," Biochim Biophys Acta. 2000;1483(2):285-93.
Ackerman et al., "Ocular itch associated with allergic conjunctivitis: latest evidence and clinical management," Ther Adv Chronic Dis. 2016;7(1):52-67.
Acland et al., "Gene therapy restores vision in a canine model of childhood blindness," Nat Genet. 2001;28(1):92-5.
Aharony et al., "Pharmacological characterization of cloned human NK-2 (neurokinin A) receptor expressed in a baculovirus/Sf-21 insect cell system," Mol Pharmacol. 1993;44(2):356-63.
Aktürk et al., "Nitric oxide and malondialdehyde levels in plasma and tissue of psoriasis patients," J Eur Acad Dermatol Venereol. 2012;26(7):833-7.
Al-Bari, "Chloroquine analogues in drug discovery: new directions of uses, mechanisms of actions and toxic manifestations from malaria to multifarious diseases," J Antimicrob Chemother. 2015;70(6):1608-21.
Al-Essa et al., "Clinical, fluorine-18 labeled 2-fluoro-2-deoxyglucose positron emission tomography (FDG PET), MRI of the brain and biochemical observations in a patient with 4-hydroxybutyric aciduria; a progressive neurometabolic disease," Brain Dev. 2000;22(2):127-31.
Al-Hasani et al., "Phosphoryl exchange is involved in the mechanism of the insulin receptor kinase," FEBS Lett. 1994;349(1):17-22.
Albano et al., "Immune response towards lipid peroxidation products as a predictor of progression of non-alcoholic fatty liver disease to advanced fibrosis," Gut. 2005;54(7):987-93.
Aldeyra Therapeutics, "Aldeyra Therapeutics Abstract Accepted at 2015 American Academy of Allergy Asthma & Immunology Annual Meeting: Novel Anti-Inflammatory Data Selected for Late-Breaking Poster Presentation," Press Release. 2014.
Aldeyra Therapeutics, "Aldeyra Therapeutics Abstract Accepted for Presentation at the 2015 Multinational Association of Supportive Care in Cancer—International Society of Oral Oncology (MASCCISOO) Annual Meeting," Press Release. 2015.
Aldeyra Therapeutics, "Aldeyra Therapeutics Abstracts Accepted for Presentation at the 2015 Annual Meeting of the Association for Research in Vision and Ophthalmology," Press Release. 2015.
Aldeyra Therapeutics, "Aldeyra Therapeutics Announces Agreement with Johnson & Johnson Innovation to Advance Novel Immune-Modulating Drugs for Systemic Inflammatory Diseases," Press Release. 2018.
Aldeyra Therapeutics, "Aldeyra Therapeutics Announces Clinical Development Update for Phase 3 Programs," Press Release. 2017.
Aldeyra Therapeutics, "Aldeyra Therapeutics Announces Collaboration With the National Organization for Rare Disorders to Enhance Awareness for Sjogren-Larsson Syndrome Patients," Press Release. 2014.
Aldeyra Therapeutics, "Aldeyra Therapeutics Announces Development Programs at 2018 Research Day," Press Release. 2018.
Aldeyra Therapeutics, "Aldeyra Therapeutics Announces First Patient Enrolled in Allergic Conjunctivitis Phase 2b Clinical Trial," Press Release. 2017.
Aldeyra Therapeutics, "Aldeyra Therapeutics Announces First Patient Enrolled in Allergic Conjunctivitis Phase 3 Clinical Trial," Press Release. 2018.

(56) References Cited

OTHER PUBLICATIONS

Aldeyra Therapeutics, "Aldeyra Therapeutics Announces First Patient Enrolled in Allergic Conjunctivitis Phase IIa Clinical Trial," Press Release. 2015.
Aldeyra Therapeutics, "Aldeyra Therapeutics Announces First Patient Enrolled in Dry Eye Disease Phase 2a Clinical Trial," Press Release. 2017.
Aldeyra Therapeutics, "Aldeyra Therapeutics Announces First Patient Enrolled in Dry Eye Disease Phase 2b Clinical Trial," Press Release. 2018.
Aldeyra Therapeutics, "Aldeyra Therapeutics Announces First Patient Enrolled in Noninfectious Anterior Uveitis Phase 3 Clinical Trial," Press Release. 2017.
Aldeyra Therapeutics, "Aldeyra Therapeutics Announces First Patient Enrolled in Noninfectious Anterior Uveitis Phase II Clinical Trial," Press Release. 2015.
Aldeyra Therapeutics, "Aldeyra Therapeutics Announces First Patient Enrolled in Sjogren-Larsson Syndrome Phase II Clinical Trial," Press Release. 2015.
Aldeyra Therapeutics, "Aldeyra Therapeutics Announces First Patient Enrolled in Sjögren-Larsson Syndrome Pivotal Phase 3 Clinical Trial," Press Release. 2018.
Aldeyra Therapeutics, "Aldeyra Therapeutics Announces Last Patient Dosed in Dry Eye Disease Phase 2a Clinical Trial," Press Release. 2017.
Aldeyra Therapeutics, "Aldeyra Therapeutics Announces Last Patient Dosed in Dry Eye Disease Phase 2b Clinical Trial," Press Release. 2018.
Aldeyra Therapeutics, "Aldeyra Therapeutics Announces Last Patient Dosed in Phase II Trial of NS2 in Patients with Allergic Conjunctivitis," Press Release. 2015.
Aldeyra Therapeutics, "Aldeyra Therapeutics Announces Last Patient Dosed in the ALLEVIATE Phase 3 Clinical Trial," Press Release. 2018.
Aldeyra Therapeutics, "Aldeyra Therapeutics Announces Positive Mesothelioma Investigator-Sponsored Clinical Trial Results Presented at The International Association for The Study of Lung Cancer 19th World Conference on Lung Cancer," Press Release. 2018.
Aldeyra Therapeutics, "Aldeyra Therapeutics Announces Positive Results from Dry Eye Disease Phase 2a Clinical Trial," Press Release. 2017.
Aldeyra Therapeutics, "Aldeyra Therapeutics Announces Positive Results from Phase 2b Dry Eye Disease Clinical Trial," Press Release. 2018.
Aldeyra Therapeutics, "Aldeyra Therapeutics Announces Positive Top-Line Results from the Phase 3 ALLEVIATE Trial in Patients with Allergic Conjunctivitis," Press Release. 2019.
Aldeyra Therapeutics, "Aldeyra Therapeutics Announces Positive Top-Line Symptom and Sign Results from Run-In Cohort of Phase 3 TRANQUILITY Trial in Dry Eye Disease," Jan. 7, 2021.
Aldeyra Therapeutics, "Aldeyra Therapeutics Announces Presentation of Novel Data on the Efficacy of ADX-102 in a Model of Succinic Semialdehyde Dehydrogenase Activity at the 2017 American Society of Human Genetics Annual Meeting," Press Release. 2017.
Aldeyra Therapeutics, "Aldeyra Therapeutics Announces Presentation of Phase 2 Allergic Conjunctivitis Results at the 2016 American College of Allergy, Asthma and Immunology Annual Scientific Meeting," Press Release. 2016.
Aldeyra Therapeutics, "Aldeyra Therapeutics Announces Presentation of Results on the Efficacy of ADX-102 in Noninfectious Anterior Uveitis at the American Uveitis Society Held at the American Academy of Ophthalmology 2017 Annual Meeting," Press Release. 2017.
Aldeyra Therapeutics, "Aldeyra Therapeutics Announces Results from Allergic Conjunctivitis Phase 2b Clinical Trial and Plans for Phase 3 Clinical Testing," Press Release. 2017.
Aldeyra Therapeutics, "Aldeyra Therapeutics Announces Third Quarter 2017 Financial Results," Press Release. 2017.

Aldeyra Therapeutics, "Aldeyra Therapeutics Launches the Aldeyra Registry for Patients with Sjögren-Larsson Syndrome," Press Release. 2017.
Aldeyra Therapeutics, "Aldeyra Therapeutics Opens Enrollment in Noninfectious Anterior Uveitis Phase II Clinical Trial," Press Release. 2015.
Aldeyra Therapeutics, "Aldeyra Therapeutics Opens Enrollment in Sjogren-Larsson Syndrome Clinical Trial and Finalizes Noninfectious Anterior Uveitis Clinical Trial Protocol," Press Release. 2015.
Aldeyra Therapeutics, "Aldeyra Therapeutics Presents Dry Eye Disease Phase 2a Clinical Trial Results at the Association for Research in Vision and Ophthalmology 2018 Annual Meeting," Press Release. 2018.
Aldeyra Therapeutics, "Aldeyra Therapeutics Presents Evidence for Aldehyde Sequestration as a Potential Therapeutic Approach in Succinic Semialdehyde Dehydrogenase Deficiency at the American Society of Human Genetics 2017 Annual Meeting," Press Release. 2017.
Aldeyra Therapeutics, "Aldeyra Therapeutics Presents Noninfectious Anterior Uveitis Phase 2 Clinical Trial Data at the Association for Research in Vision and Ophthalmology 2017 Annual Meeting," Press Release. 2017.
Aldeyra Therapeutics, "Aldeyra Therapeutics Presents Noninfectious Anterior Uveitis Phase 2 Clinical Trial Data to the American Uveitis Society Held at the American Academy of Ophthalmology 2017 Annual Meeting," Press Release. 2017.
Aldeyra Therapeutics, "Aldeyra Therapeutics Provides Update on Late-Stage Clinical Trials at 2016 Research and Development Day," Press Release. 2016.
Aldeyra Therapeutics, "Aldeyra Therapeutics Provides Update on NS2 Clinical Program," Press Release. 2015.
Aldeyra Therapeutics, "Aldeyra Therapeutics Provides Update on Ophthalmic Programs at 2019 Research & Development Day," Press Release. 2019.
Aldeyra Therapeutics, "Aldeyra Therapeutics Reaches Agreement with the US Food and Drug Administration for the Use of RASP as an Objective Sign for the Treatment of Dry Eye Disease," Press Release. 2020.
Aldeyra Therapeutics, "Aldeyra Therapeutics Schedules Conference Call and Webcast to Announce Results from Allergic Conjunctivitis Phase 2b Clinical Trial," Press Release. 2017.
Aldeyra Therapeutics, "Aldeyra Therapeutics Schedules Conference Call to Present Results of a Randomized, Double-Blind, Vehicle-Controlled Clinical Trial in Sjogren-Larsson Syndrome," Press Release. 2016.
Aldeyra Therapeutics, "Aldeyra Therapeutics Schedules Webcast and Conference Call to Announce Results from Dry Eye Disease Phase 2a Clinical Trial," Press Release. 2017.
Aldeyra Therapeutics, "Aldeyra Therapeutics Selected for Podium Presentation of Phase 2a Dry Eye Disease Results at the 2018 Association for Research in Vision and Ophthalmology (ARVO) Annual Meeting," Press Release. 2018.
Aldeyra Therapeutics, "Aldeyra Therapeutics Submits FDA IND Filing for Noninfectious Anterior Uveitis," Press Release. 2014.
Aldeyra Therapeutics, "Aldeyra Therapeutics Submits IND Filing to FDA for Clinical Testing of NS2 in Patients With Sjogren-Larsson Syndrome," Press Release. 2015.
Aldeyra Therapeutics, "Aldeyra Therapeutics to Host 2019 Research & Development Day," Press Release. 2019.
Aldeyra Therapeutics, "Aldeyra Therapeutics to Present at the 2016 SSADH Symposium," Press Release. 2016.
Aldeyra Therapeutics, "Aldeyra Therapeutics to Present Novel Data on a Potential Treatment for Sjogren-Larsson Syndrome at the 2015 Society for Inherited Metabolic Disorders Annual Meeting," Press Release. 2015.
Aldeyra Therapeutics, "Aldeyra Therapeutics to Present Novel Data on a Potential Treatment for Succinic Semi-Aldehyde Dehydrogenase Deficiency at the 2015 American Society of Human Genetics (ASHG) Annual Meeting," Press Release. 2015.
Aldeyra Therapeutics, "Aldeyra Therapeutics' Data on Lead Candidate NS2 to be Presented at Society for Investigative Dermatology 2014 Annual Meeting," Press Release. 2014.

(56) References Cited

OTHER PUBLICATIONS

Aldeyra Therapeutics, "Aldeyra Therapeutics, Inc. Announces Last Patient Dosed in Allergic Conjunctivitis Phase 2b Clinical Trial," Press Release. 2017.
Aldeyra Therapeutics, "Aldeyra Therapeutics, Inc. Announces Last Patient Dosed in Phase II Clinical Trial of Topical Dermatologic NS2 in Patients With Sjögren-Larsson Syndrome," Press Release. 2016.
Aldeyra Therapeutics, "Aldeyra Therapeutics, Inc. Receives Orphan Drug Designation from the U.S. Food and Drug Administration for ADX-102 in Sjögren-Larsson Syndrome," Press Release. 2017.
Aldeyra Therapeutics, "Phase II Allergic Conjunctivitis," Press Release. 2016.
Aldeyra Therapeutics, "Positive Results From Phase II Clinical Trial in Subjects With Noninfectious Anterior Uveitis," Press Release. 2016.
Aldeyra Therapeutics, Inc., "A Randomized, Double Masked, Clinical Study of Subjects with Dry Eye Syndrome," ClinicalTrials.gov identifier NCT03162783. First Posted May 22, 2017; https://clinicaltrials.gov/ct2/show/NCT03162783.
Aldeyra Therapeutics, Inc., "A Safety and Activity Study of NS2 in Subjects with Allergic Conjunctivitis," ClinicalTrials.gov identifier NCT02578914. First Posted Oct. 19, 2015; https://clinicaltrials.gov/ct2/show/NCT02578914.
Aldeyra Therapeutics, Inc., "A Safety and Efficacy Study of NS2 in Patients with Anterior Uveitis," ClinicalTrials.gov identifier NCT02406209. First Posted Apr. 2, 2015; https://clinicaltrials.gov/ct2/show/NCT02406209.
Aldeyra Therapeutics, Inc., "A Study of Topical NS2 Cream to Treat Ichthyosis in Sjogren-Larsson Syndrome (SLS)," ClinicalTrials.gov Identifier NCT02402309. First Posted Mar. 30, 2015; https://clinicaltrials.gov/ct2/show/NCT02402309.
Aldini et al., "Lipoxidation-derived reactive carbonyl species as potential drug targets in preventing protein carbonylation and related cellular dysfunction," ChemMedChem. 2006;1(10):1045-58.
Aldini et al., "The carbonyl scavenger carnosine ameliorates dyslipidemia and renal function in Zucker obese rats," J Cell Mol Med. 2011;15(6):1339-54.
Allergan, "Restasis® Prescribing Information," copyright 2016, revised 2017.
Amara et al., "Autoantibodies to malondialdehyde-modified epitope in connective tissue diseases and vasculitides," Clin Exp Immunol. 1995;101(2):233-8.
Ao et al., "Methyl-(beta)-Cyclodextrin Impairs the Monocyte-Adhering Ability of Endothelial Cells by Down-Regulating Adhesion Molecules and Caveolae and Reorganizing the Actin Cytoskeleton," Biol Pharm Bull. 2016;39(6):1029-34.
Apparsundaram et al., "Molecular cloning of a human, hemicholinium-3-sensitive choline transporter," Biochem Biophys Res Commun. 2000;276(3):862-7.
Ardati et al., "Interaction of [3H]orphanin FQ and 125I-Tyr14-orphanin FQ with the orphanin FQ receptor: kinetics and modulation by cations and guanine nucleotides," Mol Pharmacol. 1997;51(5):816-24.
Ashton et al., "Location of penetration and metabolic barriers to levobunolol in the corneal epithelium of the pigmented rabbit," J Pharmacol Exp Ther. 1991;259(2):719-24.
Atkinson et al., "Triazaphenanthrenes. Part VI.* Further Observations on the Widman-Stoermer and Brosche Reactions," J Chem Soc C. 1966;2053-60.
Augustin et al., "Oxidative reactions in the tear fluid of patients suffering from dry eyes," Graefes Arch Clin Exp Ophthalmol. 1995;233(11):694-8.
Axelsson et al., "Experimental colitis induced by dextran sulphate sodium in mice: beneficial effects of sulphasalazine and olsalazine," Aliment Pharmacol Ther. 1998;12(9):925-34.
Bachman and Welton, "Quinoline derivatives from 3-nitro-4-hydroxyquinoline," J Am Chem Soc. 1947;69(2):365-71.

Bacsi et al., "Effect of pollen-mediated oxidative stress on immediate hypersensitivity reactions and late-phase inflammation in allergic conjunctivitis," J Allergy Clin Immunol. 2005;116(4):836-43.
Badii, "Allergic Conjunctivitis," Healthline. 2016; Retrieved 2019: https://www.healthline.com/health/allergic-conjunctivitis.
Balci et al., "Effects of computer monitor-emitted radiation on oxidant/antioxidant balance in cornea and lens from rats," Mol Vis. 2009;15:2521-5.
Balci et al., "Investigation of oxidative stress in pterygium tissue," Mol Vis. 2011;17:443-447.
Ballard et al., "Effects of sildenafil on the relaxation of human corpus cavernosum tissue in vitro and on the activities of cyclic nucleotide phosphodiesterase isozymes," J Urol. 1998;159(6):2164-71.
Baltatzis et al., "Mycophenolate mofetil as an immunomodulatory agent in the treatment of chronic ocular inflammatory disorders," Ophthalmology. 2003;110(5):1061-5.
Bardwell et al., "Docking sites on mitogen-activated protein kinase (MAPK) kinases, MAPK phosphatases and the Elk-1 transcription factor compete for MAPK binding and are crucial for enzymic activity," Biochem J. 2003;370(Pt 3):1077-1085.
Baron et al., "[3H]MDL 105,519, a high-affinity radioligand for the N-methyl-D-aspartate receptor-associated glycine recognition site," J Pharmacol Exp Ther. 1996;279(1):62-8.
Bartoli et al., "Malondialdehyde in exhaled breath condensate as a marker of oxidative stress in different pulmonary diseases," Mediators Inflamm. 2011;2011:891752.
Bastin et al., "Salt Selection and Optimisation Procedures for Pharmaceutical New Chemical Entities," Org Proc Res Dev. 2000;4(5):427-35.
Batista et al., "Age-dependent changes in rat lacrimal gland antioxidant and vesicular related protein expression profiles," Mol Vis. 2012;18:194-202.
Batista et al., "Short-term treatment with bisphenol-A leads to metabolic abnormalities in adult male mice," PLoS One. 2012;7(3):e33814.
Baum et al., "Omega 3 fatty acid inhibition of inflammatory cytokine-mediated Connexin43 regulation in the heart," Front Physiol. 2012;3:272.
Baz et al., "Plasma reactive oxygen species activity and antioxidant potential levels in rosacea patients: correlation with seropositivity to Helicobacter pylori," Int J Dermatol. 2004;43(7):494-7.
Berge et al., "Pharmaceutical salts," J Pharm Sci. 1977;66(1):1-19.
Berkhout et al., "Cloning, in vitro expression, and functional characterization of a novel human CC chemokine of the monocyte chemotactic protein (MCP) family (MCP-4) that binds and signals through the CC chemokine receptor 2B," J Biol Chem. 1997;272(26):16404-13.
Bermudez and Grau, "Thermosensitive poloxamer-based injectables as controlled drug release platforms for veterinary use: Development and in-vitro evaluation," Int Res J Pharm Pharmacol. 2011;1(6):109-118.
Bernstein and Rando, "The specific inhibition of 11-cis-retinyl palmitate formation in the frog eye by diaminophenoxypentane, an inhibitor of rhodopsin regeneration," Vision Res. 1985;25(6):741-8.
Bernstein et al., "Mechanism of action of aromatic amines that short-circuit the visual cycle," Biochemistry. 1986;25(11):3370-7.
Bernstein et al., "Retinal toxicity associated with occupational exposure to the fish anesthetic MS-222," Am J Ophthalmol. 1997;124(6):843-4.
Bernstein et al., "Short-circuiting the visual cycle with retinotoxic aromatic amines," Proc Natl Acad Sci U S A. 1986;83(6):1632-5.
Bickett et al., "A high throughput fluorogenic substrate for interstitial collagenase (MMP-1) and gelatinase (MMP-9)," Anal Biochem. 1993;212(1):58-64.
Bignon et al., "SR146131: a new potent, orally active, and selective nonpeptide cholecystokinin subtype 1 receptor agonist. I. In vitro studies," J Pharmacol Exp Ther. 1999;289(2):742-51.
Blindauer et al., "A randomized controlled trial of etilevodopa in patients with Parkinson disease who have motor fluctuations," Arch Neurol. 2006;63(2):210-6.

(56) References Cited

OTHER PUBLICATIONS

Boldogh et al., "ROS generated by pollen NADPH oxidase provide a signal that augments antigen-induced allergic airway inflammation," J Clin Invest. 2005;115(8):2169-79.

Boner et al., "Bronchodilating activity of oral clenbuterol in asthmatic children after single administration of different dosages," Pediatr Pulmonol. 1987;3(1):34-7.

Bousquet et al., "How to design and evaluate randomized controlled trials in immunotherapy for allergic rhinitis: an ARIA-GA(2) LEN statement," Allergy. 2011;66(6):765-74.

Boyer et al., "Lipofuscin and N-retinylidene-N-retinylethanolamine (A2E) accumulate in retinal pigment epithelium in absence of light exposure: their origin is 11-cis-retinal," J Biol Chem. 2012;287(26):22276-86.

Bozkir et al., "Effect of hydroxypropyl-beta-cyclodextrin on the solubility, stability and in-vitro release of ciprofloxacin for ocular drug delivery," Acta Pol Pharm. 2012;69(4):719-24.

Bragagni et al., "Cyclodextrin complexation highly enhances efficacy of arylsulfonylureido benzenesulfonamide carbonic anhydrase inhibitors as a topical antiglaucoma agents," Bioorg Med Chem. 2015;23(18):6223-7.

Brandt et al., "The Prevalence of Non-Alcoholic Fatty Liver Disease in Patients With Inflammatory Bowel Disease," American Journal of Gastroenterology 2017;112:S542,S544.

Brenneman et al., "Cannabidiol Provides Protection from Ethanol and Ammonium toxicity in a Hippocampal Model of Hepatic Encephalopathy," 24th Annual Symposium of the International Cannabinoid Research Society, Baveno, Italy. 2014;73.

Brenneman et al., "Small molecule anticonvulsant agents with potent in vitro neuroprotection," J Mol Neurosci. 2012;47(2):368-79.

Brewitt and Sistani, "Dry eye disease: the scale of the problem," Surv Ophthalmol. 2001;45 Suppl 2:S199-202.

Bridion® (sugammadex) Injection, for intravenous use, Highlights of Prescribing Information. 2015.

Brockhaus et al., "Identification of two types of tumor necrosis factor receptors on human cell lines by monoclonal antibodies," Proc Natl Acad Sci U S A. 1990;87(8):3127-31.

Brown, "3H-batrachotoxinin-A benzoate binding to voltage-sensitive sodium channels: inhibition by the channel blockers tetrodotoxin and saxitoxin," J Neurosci. 1986;6(7):2064-70.

Brozek et al., "Grading quality of evidence and strength of recommendations in clinical practice guidelines: Part 2 of 3. The GRADE approach to grading quality of evidence about diagnostic tests and strategies," Allergy. 2009;64(8):1109-16.

Bryant et al., "A novel class of 5-HT2A receptor antagonists: aryl aminoguanidines," Life Sci. 1996;59(15):1259-68.

Bucciantini et al., "Inherent toxicity of aggregates implies a common mechanism for protein misfolding diseases," Nature. 2002;416(6880):507-11.

Buchan et al., "Characterization of three non-peptide endothelin receptor ligands using human cloned ETA and ETB receptors," Br J Pharmacol. 1994;112(4):1251-7.

Buddi et al., "Evidence of oxidative stress in human corneal diseases," J Histochem Cytochem. 2002;50(3):341-51.

Bundgaard, "(C) Means to Enhance Penetration: (1) Prodrugs as a means to improve the delivery of peptide drugs," Adv Drug Deliv Rev. 1992;8:1-38.

Burcham et al., "Aldehyde-sequestering drugs: tools for studying protein damage by lipid peroxidation products," Toxicology. 2002;181-182:229-36.

Burstein, "Preservative cytotoxic threshold for benzalkonium chloride and chlorhexidine digluconate in cat and rabbit corneas," Invest Ophthalmol Vis Sci. 1980;19(3):308-13.

Burstein, "The effects of topical drugs and preservatives on the tears and corneal epithelium in dry eye," Trans Ophthalmol Soc U K (1962). 1985;104(Pt 4):402-9.

Canonica et al., "Recommendations for standardization of clinical trials with Allergen Specific Immunotherapy for respiratory allergy. A statement of a World Allergy Organization (WAO) taskforce," Allergy. 2007;62(3):317-24.

Canonica et al., "Sub-lingual immunotherapy: World Allergy Organization Position Paper 2009," Allergy. 2009;64 Suppl 91:1-59.

Casanaro et al., "A convenient solvent system for cellulose dissolution and derivatization: Mechanistic aspects of the acylation of the biopolymer in tetraallylammonium fluoride/dimethyl sulfoxide," Carbohydr Polym. 2011;8(3):1395-402.

Casanaro et al., "Efficacy of vigabatrin intervention in a mild phenotypic expression of succinic semialdehyde dehydrogenase deficiency," JIMD Rep. 2012;2:119-23.

Cejková et al., "The role of conjunctival epithelial cell xanthine oxidoreductase/xanthine oxidase in oxidative reactions on the ocular surface of dry eye patients with Sjögren's syndrome," Histol Histopathol. 2007;22(9):997-1003.

Cesura et al., "Characterization of the binding of [3H]Ro 41-1049 to the active site of human monoamine oxidase-A," Mol Pharmacol. 1990;37(3):358-66.

Chao et al., "Co-existence of non-alcoholic fatty liver disease and inflammatory bowel disease: A review article," World J Gastroenterol. 2016;22(34): 7727-7734.

Chapple et al., "Unfolding retinal dystrophies: a role for molecular chaperones?" Trends Mol Med. 2001;7(9):414-21.

Chen et al., "Methazolamide Calcium Phosphate Nanoparticles in an Ocular Delivery System," Pharm Soc Japan, 2010; 130(3):419-24.

Cheng et al., "A synthetic peptide derived from p34cdc2 is a specific and efficient substrate of src-family tyrosine kinases," J Biol Chem. May 5, 1992;267(13):9248-56.

Chiarpotto et al., "Role of 4-hydroxy-2,3-nonenal in the pathogenesis of fibrosis," Biofactors. 2005;24(1-4):229-36.

Chicchi et al., "Alterations in receptor activation and divalent cation activation of agonist binding by deletion of intracellular domains of the glucagon receptor," J Biol Chem. 1997;272(12):7765-9.

Choi et al., "Expression of Lipid Peroxidation Markers in the Tear Film and Ocular Surface of Patients with Non-Sjogren Syndrome: Potential Biomarkers for Dry Eye Disease," Curr Eye Res. 2016;41(9):1143-9.

Choi et al., "The human serotonin 5-HT2B receptor: pharmacological link between 5-HT2 and 5-HT1D receptors," FEBS Lett. 1994;352(3):393-9.

Ciolino et al., "Effect of alcaftadine 0.25% on ocular itch associated with seasonal or perennial allergic conjunctivitis: a pooled analysis of two multicenter randomized clinical trials," Clin Ophthalmol. 2015;9:765-72.

Clark et al., "Inhibition of dexamethasone-induced cytoskeletal changes in cultured human trabecular meshwork cells by tetrahydrocortisol," Invest Ophthalmol Vis Sci. 1996;37(5):805-13.

Clinical Trials Results for Outcome Measures of Ocular Itching and Ocular Tearing (1 page) (2016).

Clinical Trials Results of Treatment with Aldehyde Trapping Compound NS2 (1 page) (2015).

Clinical Trials Results of Treatment with NS2 Topical Formulation (1 page) (2015).

Conover et al., "Thiazole Analogs of Pyridoxine," Journal of the American Chemical Society, 72(11):5221-5225 (1950).

Cooper et al., "Clinicopathologic study of dextran sulfate sodium experimental murine colitis," Lab Invest, 69(2):238-49 (Aug. 1993).

Couvineau et al., "Molecular identification and structural requirement of vasoactive intestinal peptide (VIP) receptors in the human colon adenocarcinoma cell line, HT-29," Biochem. J., 231:139-143 (1985).

Cullen et al., "Administration of the small molecule aldehyde trap NS2 in a hamster model of radiation-induced oral mucositis," ISOO 2015 Annual Meeting Abstract, Support Care Cancer, 23 (Suppl 1):S107 (Jun. 2015).

Cullen et al., "The small molecule aldehyde trap NS2 exhibits potent anti-inflammatory activity in three murine models of inflammation," AAAAI Annual Meeting Abstract, 1 page (Feb. 2015).

Davies, "Biopharmaceutical considerations in topical ocular drug delivery," Clin Exp Pharmacol Physiol, 2000; 27(7):558-62.

(56) References Cited

OTHER PUBLICATIONS

De Jong, "Age-Related Macular Degeneration," N Engl J Med, 355(14):1474-1485 (2006).
Del Valle, "Cyclodextrins and their uses: a review," Process Biochemistry, 2004; 39(9):1033-1046.
Demir et al., "Oxidative stress of intracameral lidocaine and levobupivacaine on ocular tissues," Br J Ophthalmol, 2010; 94(8):1083-7.
Demir et al., "The protective effect of alpha-lipoic acid against oxidative damage in rabbit conjunctiva and cornea exposed to ultraviolet radiation," Ophthalmologica, 2005; 219(1):49-53.
Dente et al., "Modified phage peptide libraries as a tool to study specificity of phosphorylation and recognition of tyrosine containing peptides," J. Mol. Biol., 269:694-703 (1997).
Devedjian et al., "Further characterization of human alpha 2-adrenoceptor subtypes: [31-1]RX821002 binding and definition of additional selective drugs," Eur. J. Pharmacol., 252:43-49 (1994).
Devillier et al., "The allergen challenge chamber: A valuable tool for optimizing the clinical development of pollen immunotherapy," Allergy, 2011; 66(2):163-9.
Division of AIDS, National Institute of Allergy and Infectious Diseases, National Institutes of Health, US Department of Health and Human Services, Division of AIDS (DAIDS) Table for Grading the Severity of Adult and Pediatric Adverse Events, V2.0, 33 pages. (Nov. 2014).
Dolmotova et al., "Cardiomyocyte ATP release through pannexin 1 aids in early fibroblast activation," Am. J. Physiol Heart Circ Physiol 303(10):H1208-1218 (2012).
Dorje et al., "Antagonist binding profiles of five cloned human muscarinic receptor subtypes," J. Pharmacol. Exp. Ther., 256:727-733 (1991).
Dowling, "Neural and Photochemical Mechanisms of Visual Adaptation in the Rat," Journal of General Physiology, 46(6):1287-1291 (1963).
Drysdale et al., "Complex Promoter and Coding Region Beta 2-adrenergic Receptor Haplotypes Alter Receptor Expression and Predict in vivo Responsiveness," Proc Natl Acad Sci USA, 97(19):10483-10488 (2000).
Egger, et al., "Keratinocyte growth factor ameliorates dextran sodium sulfate colitis in mice," Dig Dis Sci, 44(4): 836-44 (Apr. 1999).
Ellis et al., "Multiple Doses of Trodusquemine Improve Glucose Tolerance in Type 2 Diabetic Subjects," 69th Scientific Sessions of the American Diabetes Association, Abstract No. 2071-PO (2009).
Ellman et al., "A new and rapid colorimetric determination of acetylcholinesterase activity," Biochem. Pharmacol., 7: 88-95 (1961).
Erdos et al, "Neutral endopeptidase 24.11 (enkephalinase) and related regulators of peptide hormones," FASEB J. 3:145 (1989).
Ermolieff et al., "Proteolytic activation of recombinant promemapsin 2 (pro-beta-secretase) studied with new fluorogenic substrates," Biochemistry, 39:12450-12456 (2000).
Escalera et al., "Succinic semialdehyde dehydrogenase deficiency: decrease in 4-OH-butyric acid levels with low doses of vigabatrin," An Pediatr (Barc). 72(2):128-32 (2010).
Esterbauer et al., "Chemistry and Biochemistry of 4-Hydroxynonenal, Malonaldehyde and Related Aldehydes," Free Radic Biol Med, 1991; 11:81-128.
Everest-Todd, "Topical Application of Cyclodextrin Ethers in the Control of Pain," Proceedings of the Eighth International Symposium on Cyclodextrins, pp. 495-498 (1998).
Farid et al., "Detection of corneal fibrosis by imaging second harmonic-generated signals in rabbit corneas treated with mitomycin C after excimer laser surface ablation," Invest Ophthalmol Vis Sci. 2008;49(10):4377-83.
FDA, "Bam R59: Phosphate-Buffered Saline (PBS), pH 7.4," Jan. 2001, retrieved online at <http://www.fda.gov/Food/FoodScienceR.esearch/LaboratoxyMethods/ucm062268.htm> on Apr. 18, 2015 (1 page).
Feighner et al., "Receptor for motilin identified in the human gastrointestinal system," Science, 284:2184-2188 (1999).
Fernandes et al., "Characterization of angiotensin-converting enzymes 1 and 2 in the soleus and plantaris muscles of rats," Braz J Med Biol Res., 43:837-842 (2010).
Ferry et al., "Binding of prostaglandins to human PPAR?: Tool assessment and new natural ligands," Eur. J. Pharmacol., 417:77-89 (2001).
Feve et al., "Transcriptional down-regulation by insulin of the beta 3-adrenergic receptor expression in 3T3-F442A adipocytes: a mechanism for repressing the cAMP signaling pathway," Proc Natl Acad Sci USA. 91:5677 (1994).
Fiske et al., "The Colormetric Determination of Phosphorus," J. Biol. Chem., 66:375-400 (1925).
Fitzmaurice et al., "Aldehyde dehydrogenase inhibition as a pathogenic mechanism in Parkinson disease," Proc. Natl Acad Sci U.S.A, 110(2):636-641 (2013).
Ford et al., "Pharmacological pleiotropism of the human recombinant alpha1A-adrenoceptor: implications for alphal-adrenoceptor classification," Brit. J. Pharmacol., 121:1127-1135 (1997).
Fowler et al., "Coloured Complexes of all-trans-retinal with Benzocaine and Other Local Anesthetics," J Photochem Photobiol B, 8(2):183-188 (1991).
Frantz et al., "The Activation State of p38 Mitogen-Activated Protein Kinase Determines the Efficiency of ATP Competition for Pyridinylimidazole Inhibitor Binding," Biochemistry, 37:13846-13853 (1998).
Friesen et al., "Optimization of a Tertiary Alcohol Series of Phosphodiesterase-4 (PDE4) Inhibitors: Structure-Activity Relationship Related to PDE4 Inhibition and Human Ether-a-go-go Related Gene Potassium Channel Binding Affinity," J. Med. Chem., 46(12):2413-2426 (2003).
Fuchs et al., "Functional characterization of three mutations of the endothelin B receptor gene in patients with Hirschsprung's disease: evidence for selective loss of Gi coupling," Mol. Med., 7:115-124 (2001).
Fukunaga et al., "Single nucleotide polymorphism of human platelet-activating factor receptor impairs G-protein activation," J. Biol. Chem., 276:43025-43030 (2001).
Full 1H NMR assignment for RAL-NS2 in CDCIJ, submitted to Japanese Patent Office Mar. 1, 2012.
Ganapathy et al., "Molecular and ligand-binding characterization of the sigma-receptor in the Jurkat human T lymphocyte cell line," JPET, 289:251-260 (1999).
Gasper et al., "2-Hydroxypropyl-beta-cyclodextrin (HPβCD) reduces age-related lipofuscin accumulation through a cholesterol-associated pathway," Scientific Reports, 2017; 7(2197):1-7.
Gibson et al., "Stable isotope dilution analysis of 4-hydroxybutyric acid: an accurate method for quantification in physiological fluids and the prenatal diagnosis of 4-hydroxybutyric aciduria," Biomed Environ Mass Spectrom., 19(2):89-93 (1990).
Gibson et al., "Stable-isotope dilution analysis of D- and L-2-hydroxyglutaric acid: application to the detection and prenatal diagnosis of D- and L-2-hydroxyglutaric acidemias," Pediatr Res., 34(3):277-80 (1993).
Gibson et al., "The Aldehyde Trap NS2 Mitigates Dense Haze in a Rabbit Model of Photorefractive Keratectomy" ARVO Annual Meeting Abstract, 1 page (Jun. 2015).
Godard et al., "Sur les orthoamino formyl quinoleines, nouveaux synthons heterocycliques," J Heterocyclic Chem, 17(3):465-473 (1980).
Goldstein et al., "A Phase 2 Exploratory Study of a Novel Interleukin-1 Receptor Inhibitor (EBI-005) in the Treatment of Moderate-to-Severe Allergic Conjunctivitis," Eye Contact Lens, 2015; 41(3):145-55.
Gole et al., "Plasma Proteins Modified by Tyrosine Nitration in Acute Respiratory Distress Syndrome," Am J Physiol Lung Cell Mol Physiol, 2000, vol. 278, pp. L961-L967.
Gomez, "Dimethyltin(IV) 2,6-disubstituted pyridine complexes," J. Organometallic Chemistry, 672(2):115-122 (2003).
Good, "Measuring field loss in children administered vigabatrin: a problem in search of a solution," JAAPOS. 15(5):411-2 (2011).
Gopalakrishnan et al., "Stable expression, pharmacologic properties and regulation of the human neuronal nicotinic acetylcholine alpha 4 beta 2 receptor," J. Pharmacol. Exp. Ther., 276:289-297 (1996).

(56) References Cited

OTHER PUBLICATIONS

Gould et al., "[3H]nitrendipine-labeled calcium channels discriminate inorganic calcium agonists and antagonists," Proc. Natl. Acad. Sci. U.S.A., 79:3656-3660 (1982).
Grandy et al., "Cloning of the cDNA and gene for a human D2 dopamine receptor," Proc. Natl. Acad. Sci. U.S.A., 86:9762-9766 (1989).
Green et al., "Characterization of [(3)H]-CGP54626A binding to heterodimeric GABA(B) receptors stably expressed in mammalian cells," Brit. J. Pharmacol., 131:1766-1774 (2000).
Green et al., "Influence of Various Agents on Corneal Permeability," American Journal of Ophthalmology, 1971; 72(5):897-905.
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950).
Gromachevskaya et al., "4H-3,1-benzoxazines. 2. Synthesis of 2,4-substituted 1 2-dihydro-4H-3,1-benzoxazines," Chemistry of Heterocyclic Compounds, 24(6):692-697 (Jun. 1988).
Grotto et al., "Importance of the lipid peroxidation biomarkers and methodological aspects for malondialdehyde quantification," Quim Nova, 2009; 32(1):169-174.
Halilovic et al., "ADX-103, a Novel Small Molecule Aldehyde Sequestering Agent, Decreases Retinal Edema and Inflammation in a Rat Model of Diabetic Macular Edema," ARVO Annual Meeting Abstract, 2 pages (Jul. 2018).
Hampson et al., "Cannabidiol and (-)Delta9-tetrahydrocannabinol are neuroprotective antioxidants," Proc. Nat. Acad. Sci 95:8268-8273 (1998).
Hassan et al., "Oxidative stress in systemic lupus erythematosus and rheumatoid arthritis patients: relationship to disease manifestations and activity," International Journal of Rheumatic Diseases, 14(1):325-331 (2011).
Herbort et al., "Endotoxin-induced uveitis in the rat," Graefe's Arch Clin Exp Ophthalmol, 1988; 226:553-8.
Hessen et al., "Dry Eye: an Inflammatory Ocular Disease," J Ophthalmic Vis Res, 2014; 9(2):240-250.
Heuillet et al., "Characterization of a Human NK1 Tachykinin Receptor in the Astrocytoma Cell Line U 373 MG," J. Neurochem., 60:868-876 (1993).
Highlights of Prescribing Information, Bridion® (sugammadex) Injection, for intravenous use, Initial U.S. Approval: 2015, Last Revised Dec. 2015 (19 pages).
Hogema et al., "Pharmacologic rescue of lethal seizures in mice deficient in succinate semialdehyde dehydrogenase," Nat Genet. 29:212-16 (2001).
Hom et al., "Allergic conjunctivitis and dry eye syndrome," Ann Allergy Asthma Immunol, 2012; 108(3):163-6.
Hong et al., "Laboratory Scale Production of Injectable Liposomes By Using Cell Disruptor . . . ," Journal of Pharmaceutical Investigation, 2015, vol. 45, pp. 73-78.
Hope et al., "Characterization of a human 5-hydroxytryptamine3 receptor type A (h5-HT3R-AS) subunit stably expressed in HEK 293 cells," Brit. J. Pharmacol., 118:1237-1245 (1996).
Horner et al., "Analogs of 3-Amino-7-chloro-1,2,4-benzotriazine 1-Oxide as Antimalarial Agents," J. Med. Chem., 11(5):946-949 (1968).
Hoyer et al., "Characterization of the 5-HT1B recognition site in rat brain: binding studies with (-)[125I]iodocyanopindolol," Eur. J. Pharmacol., 118:1-12 (1985).
Huang et al., "Characterization of Calcium Phosphate Nanoparticles Based on a PEGylated Chelator for Gene Delivery," ACS Appl Mater Interfaces, 9:10435?10445 (Mar. 2017).
Huang et al., "Identification of human Ether-a-go-go related gene modulators by three screening platforms in an academic drug-discovery setting," Assay Drug Dev Technol., 8(6):727-42 (2010).
Huang et al., "Novel peptide inhibitors of angiotensin-converting enzyme 2," J. Biol. Chem., 278:15532-15540 (2003).
Hubbard, "Geometrical Isomerization of Vitamin A, Retinene and Retinene Oxime," Journal of the American Chemical Society, 78(18):4662-4667 (1956).
Hugues et al., "Preparation of a pure monoiodo derivative of the bee venom neurotoxin apamin and its binding properties to rat brain synaptosomes," J. Biol. Chem., 257:2762-2769 (1982).
Hurd et al., "Reaction of Propiolactone with Aniline Derivatives," Journal of the American Chemical Society, 74(23):5889-5893 (1952).
Inoue et al., "Filter-binding assay procedure for thyroid hormone receptors," Anal Biochem. 134(1):176 (1983).
Iriyama et al., "A2E, a pigment of the lipofuscin of retinal pigment epithelial cells, is an endogenous ligand for retinoic acid receptor," J Biol Chem., 283(18):11947-53 (2008) Epub Mar. 6, 2008.
Irons, "Fluvoxamine in the treatment of anxiety disorders," Neuropsychiatr Dis Treat. 2005;1(4):289-99.
Ishida et al., "Stabilization of calmodulin-dependent protein kinase II through the autoinhibitory domain," J. Biol. Chem., 270:2163-2170 (1995).
Ito et al., "A Medium-Term Rat Liver Bioassay for Rapid in vivo Detection of Carcinogenic Potential of Chemicals," Cancer Science, 94(1):3-8 (2003).
Itokawa et al., "Antiangiogenic effect by SU5416 is partly attributable to inhibition of Flt-1 receptor signaling," Mol. Cancer Ther., 1:295-302 (2002).
Jacobs et al., "Responses to ragweed pollen in a pollen challenge chamber versus seasonal exposure identify allergic rhinoconjunctivitis endotypes," J. Allergy Clin. Immunol., 2012; 130(1):122-7.
Jafari et al., "Evaluation of plasma, erythrocytes, and bronchoalveolar lavage fluid antioxidant defense system in sulfur mustard-injured patients," Clin Toxicol (Phila)., 48(3):184-92 (2010).
Janowski et al., "Structural requirements of ligands for the oxysterol liver X receptors LXRalpha and LXRbeta," Proc. Natl. Acad. Sci. USA, 96:266-271 (1999).
Jarrett et al., "Mitochondrial DNA damage and impaired base excision repair during epileptogenesis," Neurobiology of Disease, 30(1):130-138 (2008).
Jellinger et al., "American Association of Clinical Endocrinologists and American College of Endocrinology Guidelines for Management of Dyslipidemia and Prevention of Cardiovascular Disease," Endocr Pract. 2017;23(Suppl 2):1-87.
Ji et al., "Exploration of diverse hinge-binding scaffolds for selective Aurora kinase inhibitors," Bioorg. & Med. Chem. Let. 22:4528 (2012).
Johannsdottir et al., "Development of a Cyclodextrin-Based Aqueous Cyclosporin A Eye Drop Formulations," International Journal of Pharmaceutics, 2015; 493(1-2):86-95.
Johnson et al., "2-Hydroxypropyl-β-Cyclodextrin Removes All-Trans Retinol from Frog Rod Photoreceptors in a Concentration-Dependent Manner," Journal of Ocular Pharmacology and Therapeutics, 2010; 26(3):245-248.
Joseph et al., "Binding of (-)-[3H]-CGP12177 at two sites in recombinant human beta 1-adrenoceptors and interaction with beta-blockers," Naun.-Sch. Arch. Pharm., 369:525-532 (2004).
Kam et al., "Topical Cyclodextrin Reduces Amyloid Beta and Inflammation Improving Retinal Function in Ageing Mice," Experimental Eye Research, 2015; 135:59-66.
Kamino et al., "Deficiency in mitochondrial aldehyde dehydrogenase increases the risk for late-onset Alzheimer's disease in the Japanese population," Biochemical and Biophysical Research Communications, 273(1):192-196 (2000).
Karahashi et al., "Changes of caspase activities involved in apoptosis of a macrophage-like cell line J774.1/JA-4 treated with lipopolysaccharide (LPS) and cycloheximide," Biol. Pharm. Bull., 23:140-144 (2000).
Karan et al., Lipofuscin Accumulation, Abnormal Electrophysiology, and Photoreceptor Degeneration in Mutant ELOVL4 Transgenic Mice: A Model for Macular Degeneration, Proc Natl Acad Sci USA, 102(11):4164-4169 (2005).
Katugampola et al., "[(125)I]-(Pyr(1))Apelin-13 is a novel radioligand for localizing the APJ orphan receptor in human and rat tissues with evidence for a vasoconstrictor role in man," Brit. J. Pharmacol., 132:1255-1260 (2001).

(56) References Cited

OTHER PUBLICATIONS

Keister et al., "Inflammatory Bowel Disease and Irritable Bowel Syndrome Similarities and Differences," Crohn's & Colitis Foundation of America 2014.
Kenney et al., "The Cascade Hypothesis of Keratoconus," Contact Lens & Ant Eye, 26:139-146 (2003).
Keri, "Rosacea," Merck Manual, Professional Version, https://www.merckmanuals.com/professional/dermatologic-disorders/acne-and-related-disorders/rosacea, 7 pages (2017).
Knapp et al., "Intraocular Availability of Topically Applied Mycophenolate Mofetil in Rabbits," J. Ocul. Pharmacol. Ther., 2003; 19(2):181-192.
La Rosa et al., "Allergic conjunctivitis: a comprehensive review of the literature," Ital J Pediatr, 2013; 39:18.
Landor et al., "Allenes. Part 49, 4-Amino-2-(1-hydroxyalkyl)quinolones from Phenylhydroxylamine and Allenic Nitrites," J Chem Soc Perkin Trans 1, pp. 251-254 (1989).
Langin et al., "[3H]RX821002: a new tool for the identification of alpha 2A-adrenoceptors," Eur. J. Pharmacol., 167: 95-104 (1989).
Lankin et al., "Role of Oxidative Stress in the Genesis of Atherosclerosis and Diabetes Mellitus: A Personal Look Back on 50 Years of Research," Curr. Aging Sci. 10:18 (2017).
Le et al., "Ligand binding and functional properties of human angiotensin AT1 receptors in transiently and stably expressed CHO-K1 cells," Eur. J. Pharmacol., 513:35-45 (2005).
Lee et al., "Human recombinant soluble guanylyl cyclase: expression, purification, and regulation," Proc. Natl. Acad. Sci. USA, 97(20):10763-10768 (2000).
Lee et al., "The human brain cholecystokinin-B/gastrin receptor. Cloning and characterization," J. Biol. Chem., 268: 8164-8169 (1993).
Leibundgut et al., "Oxidation-specific epitopes and immunological responses: Translational biotheranostic implications for atherosclerosis," Current Opinion in Pharmacology, 13(2):168-179 (2013).
Leonardi et al., "Correlation Between Conjunctival Provocation Test (CPT) and Systemic Allergometric Tests in Allergic Conjunctivitis," Eye, 1990; 4:760-764.
Leonardi, "Allergy and allergic mediators in tears," Exp. Eye Res., 2013; 117:106-17.
Leurs et al., "Pharmacological characterization of the human histamine H2 receptor stably expressed in Chinese hamster ovary cells," Brit. J. Pharmacol., 112: 847-854 (1994).
Levey et al., "A new equation to estimate glomerular filtration rate," Ann Intern Med. 2009;150(9):604-12.
Levin et al., "The myocardium-protective Gly-49 variant of the beta 1-adrenergic receptor exhibits constitutive activity and increased desensitization and down-regulation," J. Biol.Chem., 277:30429-30435 (2002).
Lewin et al., "meta- and para-isothiocyanato-t-butylbicycloorthobenzoate: irreversible ligands of the gamma-aminobutyric acid-regulated chloride ionophore," Mol. Pharmacol., 35:189-194 (1989).
Li et al., "Effect of Vitamin A Supplementation on Rhodopsin Mutants Threonine-17→ Methionine and Proline-347→ Serine in Transgenic Mice and in Cell Cultures," Proc Natl Acad Sci USA, 95(20):11933-11938 (1998).
Liang et al., "Ocular safety of cationic emulsion of cyclosporine in an in vitro corneal wound-healing model and an acute in vivo rabbit model," Mol Vis, 2012; 18:2195-204.
Liu et al., "Comparison of human, mouse, rat, and guinea pig histamine H4 receptors reveals substantial pharmacological species variation," J. Pharmacol. Exp. Ther., 299:121-130 (2001).
Loftsson et al., "Cyclodextrin Microparticles for Drug Delivery to the Posterior Segment of the Eye: Aqueous Dexamethasone Eye Drops," Journal of Pharmacy and Pharmacology, 2007; 59(5):629-635.
Loftsson et al., "Cyclodextrins in Eye Drop Formulations: Enhanced Topical Delivery of Corticosteroids to the Eye," Acta Ophthalmologica Scandinavica, 2002; 80(2):144-150.
Lopachin et al., "Molecular mechanisms of aldehyde toxicity: a chemical perspective," Chem Res Toxicol, 2014; 27(7):1081-91.
Lovenberg et al., "Cloning and functional expression of the human histamine H3 receptor," Mol. Pharmacol., 55:1101-1107 (1999).
Lukas, R.J., "Characterization of curaremimetic neurotoxin binding sites on membrane fractions derived from the human medulloblastoma clonal line, T15671," J. Neurochem., 46:1936-1941 (1986).
Luthin et al., "Characterization of two affinity states of adenosine A2a receptors with a new radioligand, 2-[2-(4-amino-3-[125l]iodophenyl)ethylamino]adenosine," Mol. Pharmacol., 47:307-313 (1995).
MacDonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).
MacDonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).
MacDonald et al., "Molecular characterization of the melanin-concentrating hormone/receptor complex: identification of critical residues involved in binding and activation," Mol. Pharmacol., 58:217-225 (2000).
MacDonald et al., "Novel Small Molecule Aldehyde Sequestering Agents Demonstrate Broad Therapeutic Potential for Ocular Inflammation," ARVO Annual Meeting Abstract, 2 pages (Jul. 2018).
MacDonald et al., "The novel aldehyde trap, ADX-102, reduces inflammation-mediated lung infiltrate in a mouse model of LPS-induced acute lung injury," 13th World Congress on Inflammation Abstract, p. 192 (Jul. 2017).
MacKenzie et al., "Characterization of the human dopamine D3 receptor expressed in transfected cell lines," Eur. J. Pharmacol., 266:79-85 (1994).
Maeda et al., "Involvement of All-trans-retinal in Acute Light-induced Retinopathy of Mice," J Biol Chem, 284(22):15173-83 (May 2009).
Maeda et al., "Primary amines protect against retinal degeneration in mouse models of retinopathies," Nat Chem Biol, 2011; 8(2):170-178.
Maguire et al., "Orphan-receptor ligand human urotensin II: receptor localization in human tissues and comparison of vasoconstrictor responses with endothelin-1," Brit. J. Pharmacol., 131:441-446 (2000).
Malondialdehyde, Wikipedia, 2008, retrieved from the internet on Aug. 4, 2021 at https://en.wikipedia.org/wiki/Malondialdehyde.
Malondialdehyde, Wikipedia. Edited 2020; Accessed 2021: https://en.wikipedia.org/w/index.php?title=Malondialdehyde&oldid=993228459.
Mandell et al., "The Aldehyde Trap NS2 Reduces Ocular Inflammation in an Endotoxin-Induced Model in Rats," Investigative ophthalmology & visual science. 2015; 56(7):3095.
Mantey et al., "Discovery of a high affinity radioligand for the human orphan receptor, bombesin receptor subtype 3, which demonstrates that it has a unique pharmacology compared with other mammalian bombesin receptors," J. Biol. Chem., 272:26062-26071 (1997).
Marnett, "Oxy radicals, lipid peroxidation and DNA damage," Toxicology, 181-182:219-222 (2002).
Martin et al., "Molecular cloning and functional characterization of murine cysteinyl-leukotriene 1 (CysLT(1)) receptors.," Biochem. Pharmacol., 62:1193-1200 (2001).
Matern et al., "Seizures in a boy with succinic semialdehyde dehydrogenase deficiency treated with vigabatrin (gamma-vinyl-GABA)," J Inherit Metab Dis., 19(3):313-8 (1996).
Mathew et al., "Updates in the management of diabetic macular edema," J Diabetes Res. 2015; 2015:794036.
Maurice et al., "Advances in targeting cyclic nucleotide phosphodiesterases," Nat Rev Drug Discov., 2014; 13:290-314.
McCord et al., "Superoxide dismutase. An enzymic function for erythrocuprein (hemocuprein).," J. Biol. Chem., 1969; 244: 6049-6055.
McGinnity et al., "Evaluation of fresh and cryopreserved hepatocytes as in vitro drug metabolism tools for the prediction of metabolic clearance." Drug Metab. Dispos., 32(11):1247-1253 (2004).
McLaurin et al., "Phase 3 Randomized Double-Masked Study of Efficacy and Safety of Once-Daily 0.77% Olopatadine Hydrochlo-

(56) References Cited

OTHER PUBLICATIONS ride Ophthalmic Solution in Subjects with Allergic Conjunctivitis Using the Conjunctival Allergen Challenge Model," Clinical Science, 2015; 34(10):1245-1251.

Medline Plus. Macular Degeneration—age-related. (6 pages) (2013).

Meijer et al., "Biochemical and cellular effects of roscovitine, a potent and selective inhibitor of the cyclin-dependent kinases cdc2, cdk2 and cdk5," Eur. J. Biochem., 243:527-536 (1997).

Meng et al., "Cloning and pharmacological characterization of a rat kappa opioid receptor," Proc. Natl. Acad. Sci. U.S.A., 90:9954-9958 (1993).

Merck Sharp & Dohme Corp., "Bridion® (sugammadex) Injection Prescribing Information, for intravenous use," Highlights of Prescribing Information. 2015.

Mialet et al., "Isolation oftheserotoninergic 5-HT4(e) receptor from human heart and comparative analysis of its pharmacological profile in C6-glial and CHO cell lines," Brit. J. Pharmacol., 129:771-781 (2000).

Miceli et al., "Efficacy of keratinocyte growth factor-2 in dextran sulfate sodium-induced murine colitis," J Pharmacol Exp Ther, 290(1):464-71 (Jul. 1999).

Mishra et al., "Recent Patents and Emerging Therapeutics in the Treatment of Allergic Conjunctivitis," Recent Pat. Inflamm. Allergy Drug Discov.; 2011; 5(1):26-36.

Mittl et al., "Structure of recombinant human CPP32 in complex with the tetrapeptide acetyl-Asp-Val-Ala-Asp fluoromethyl ketone," J. Biol. Chem., 272:6539-6547 (1997).

Monaghan et el., "The distribution of [3H]kainic acid binding sites in rat CNS as determined by autoradiography," Brain Res., 252:91-100 (1982).

Monsma et al., "Cloning and expression of a novel serotonin receptor with high affinity for tricyclic psychotropic drugs," Mol. Pharmacol., 43:320-327 (1993).

Mulheron et al., "Human 5-HT1A receptor expressed in insect cells activates endogenous G(o)-like G protein(s)," J. Biol. Chem., 269:12954-12962 (1994).

Muller-Enoch et al., "[6.7-Dihydroxycoumarin (Aesculetin) as a substrate for catechol-o-methyltransferase (author's transl)]," Z. Naturforsch., 31:280-284 (1976).

Munro et al., "Molecular characterization of a peripheral receptor for cannabinoids," Nature, 365:61-65 (1993).

Murphy et al., "Characterization of quisqualate recognition sites in rat brain tissue using DL-[3H]alpha-amino-3-hydroxy-5-methylisoxazole-4-propionic acid (AMPA) and a filtration assay," Neurochem. Res., 12:775-781 (1987).

Na et al., "Molecular profiling of a 6-hydroxydopamine model of Parkinson's disease," Neurochem Res. 2010;35(5):761-72.

Nagai et al., Improved corneal toxicity and permeability of tranilast by the preparation of ophthalmic formulations containing its nanoparticles, J Oleo Sci, 2014; 63(2):177-86.

Nagase et al., "Design and characterization of a fluorogenic substrate selectively hydrolyzed by stromelysin 1 (matrix metalloproteinase-3), "J. Biol. Chem., 269:20952-20957 (1994).

Nakamura et al., "Involvement of Oxidative Stress on Corneal Epithelial Alterations in a Blink-Suppressed Dry Eye," Investigative Ophthalmology and Visual Science, 2007; 48(4):1552-1558.

Negre-Salvayre et al., "Advanced Lipid Peroxidation End Products in Oxidative Damage to Proteins. Potential Role in Diseases and Therapeutic Prospects for the Inhibitors," Br J Pharmacol, 2008; 153(1):6-20.

Nema et al., "Excipients and Their Use in injectable Products," PDA J Pharm Sci Technol, 51(4):166-171 (1997).

Nerurkar et al., "Beta-Arylglutaconic Acids. II. Imides of Certain Beta-Arylglutaconic and Glutaric Acids," J Org Chem, 24(12):2055-2056 (1959).

Nielsen and Bundgaard, "Glycolamide esters as biolabile prodrugs of carboxylic acid agents: synthesis, stability, bioconversion, and physicochemical properties," J Pharm Sci. 1988;77(4):285-98.

Niwa et al., "Protein oxidative damage in the stratum corneum: Evidence for a link between environmental oxidants and the changing prevalence and nature of atopic dermatitis in Japan," Br J Dermatol., 2003; 149:248.

Nociari et al., "Beta cyclodextrins bind, stabilize, and remove lipofuscin bisretinoids from retinal pigment epithelium," Proc Natl Acad Sci U.S.A., 2014; E1402-E1408.

Noorwez et al., "Pharmacological Chaperone-mediated in Vivo Folding and Stablization of the P23H-Opsin Mutant Associated with Autosomal Dominant Retinitis Pigmentosa," J Biol Chem, 278:14442-14450 (2003).

O'Brien et al., "Aldehyde Sources, Metabolism, Molecular Toxicity Mechanisms, and Possible Effects on Human Health," Crit Rev Toxicol, 2005; 35:609-662.

O'Regan et al., "Filaggrin in atopic dermatitis," J Allergy Clin Immunol. 2009;124(3 Suppl 2):R2-6.

Obourn et al., "Hormone- and DNA-binding mechanisms of the recombinant human estrogen receptor," Biochemistry 32(24):6229 (1993).

Okayasu et al., "A novel method in the induction of reliable experimental acute and chronic ulcerative colitis in mice," Gastroenterology. 1990;98(3):694-702.

Organisciak et al., "Susceptibility to Retinal Light Damage in Transgenic Rats with Rhodopsin Mutations," Invest Ophthalmol Vis Sci, 44(2):486-492 (2003).

Ousler et al., "Use of the Controlled Adverse Environment (CAE) in Clinical Research: A Review," Opthalmology and Therapy, Sep. 27, 2017, vol. 6, pp. 263-276.

Pacholczyk et al., "Expression cloning of a cocaine- and antidepressant-sensitive human noradrenaline transporter," Nature, 350:350-354 (1991).

Pal et al., "Sulfur mustard analog induces oxidative stress and activates signaling cascades in the skin of SKH-1 hairless mice," Free Radic Biol Med., 47(11):1640-51 (2009).

Palchaudhuri et al., "Corticotropin-releasing factor receptor type 1 from Tupaia belangeri-cloning, functional expression and tissue distribution," Eur. J. Biochem., 258:78-84 (1998).

Parish et al., "Isolation and One-Step Preparation of A2E and iso-A2E, Fluorophores from Human Retinal Pigment Epithelium," Proc Natl Acad Sci USA, 95(25):14609-14613 (1998).

Park et al., "Modulation of Acute Inflammation and Keratocyte Death by Suturing, Blood, and Amniotic Membrane in PRK," Invest. Opthalmol Vis Sci. 2000;41(10):2906-14.

Park et al., "Homogeneous proximity tyrosine kinase assays: scintillation proximity assay versus homogeneous time-resolved fluorescence," Anal. Biochem., 269:94-104 (1999).

Parracho et al., "Differences between the gut microflora of children with autistic spectrum disorders and that of healthy children," Journal of Medical Microbiology, 54:987-991 (2005).

Patel C.Y., "Subtype selectivity of peptide analogs for all five cloned human somatostatin receptors (hsstr 1-5)," Endocrinology, 135:2814-2817 (1994).

Pellock, "Balancing clinical benefits of vigabatrin with its associated risk of vision loss," Acta Neurologica. Scandinavica. Supplementum., 124(s192):83-91 (2011).

Petroski et al., "Selective labeling of embryonic neurons cultured on astrocyte monolayers with 5(6)-carboxyfluorescein diacetate (CFDA)," Journal of Neuroscience Methods, 52(1):23-32 (1994).

Pfaar et al., "Perspectives in allergen immunotherapy: 2017 and beyond," Allergy, 2018; 73(Suppl 104):5-23.

Pontikis et al., "Cyclodextrin alleviates neuronal storage of cholesterol in Niemann-Pick C disease without evidence of detectable blood-brain barrier permeability," Journal of Inherited Metabolic Disease, 2013; 36(3):491-498.

Pozzi et al., "Modification of Collagen IV by Glucose or Methylglyoxal Alters Distinct Mesangial Cell Function," Journal of the American Society of Nephrology, 20:2119-2125 (2009).

Pred Forte Prescribing Information, Allergan, 5 pages (2017).

Pristupa et al., "Pharmacological heterogeneity of the cloned and native human dopamine transporter: disassociation of [3H]WIN 35,428 and [3H]GBR 12,935 binding.," Mol. Pharmacol., 45:125-135 (1994).

(56) References Cited

OTHER PUBLICATIONS

Pruneau et al., "LF 16.0335, a novel potent and selective nonpeptide antagonist of the human bradykinin B2 receptor," Brit. J. Pharmacol., 125:365-372 (1998).
Pubchem, 1824609-67-7, SID 333824451, Apr. 24, 2017 (6 pages).
Pubchem, 2-(3-Aminoquinolin-2-yl)propan-2-ol, CID 117758222, Feb. 23, 2016, modified Jun. 13, 2020 (11 pages).
Pubchem, SCHEMBL16316728, CID 117758222, Feb. 23, 2016, modified Sep. 30, 2017 (13 pages).
Roberts et al., "Experimental Organic Chemistry—A Miniscale Approach," copyright 1994 by Saunders College Publishing, pp. 580-581 and 584-586.
Roche, "Tween 20," Sigma-Aldrich Datasheet. Retrieved Nov. 19, 2020: https://www.sigmaaldrich.com/catalog/product/roche/11332465001?lang=en&region=US# :~: text=Tween%2020%>.
Rohrer et al., "Cloning and characterization of a fourth human somatostatin receptor," Proc. Natl. Acad. Sci. U.S.A., 90:4196-4200 (1993).
Roumen et al., "Serum Lipofuscin as a Prognostic Indicator of Adult Respiratory Distress Syndrome and Multiple Organ Failure," British Journal of Surgery, 1994, vol. 81, pp. 1300-1305.
Rønborg et al., "Exposure chamber for allergen challenge. The development and validation of a new concept," Allergy, 1996; 51(2):82-8.
Sahi et al., "Hepatocytes as a tool in drug metabolism, transport and safety evaluations in drug discovery." Current Drug Discov. Technol., 7(3):188-198 (2010).
Salvatore et al., "Molecular cloning and characterization of the human A3 adenosine receptor," Proc. Natl. Acad. Sci. U.S.A., 90:10365-10369 (1993).
Samsonov et al., "Impact of Atherosclerosis- and Diabetes-Related Dicarbonyls on Vascular Endothelial Permeability: A Comparative Assessment," Oxid. Med. Cell Longev. Article 1625130 (2017).
Sanchez et al., "Allergic Conjunctivitis," J Investig Allergol Clin Immunol., 2011; 21(2):1-19.
Sandikci et al., "Lipid Peroxidation and Antioxidant Defence System in Patients with Active or Inactive Behcet's Disease," Acta Derm Venereol, 2003; 83:342-346.
Sarafian et al., "Synergistic cytotoxicity of Delta(9)-tetrahydrocannabinol and butylated hydroxyanisole," Toxicology Letters, 133(2-3):171-179 (2002).
Sarfare et al., "Biocompatibility of a Synthetic Biopolymer for the Treatment of Rhegmatogenous Retinal Detachment," J Clin Exp Ophthalmol. 2015;6(5):475.
Sarup et al., "Resolution of high and low affinity progesterone receptors from human breast carcinoma T47D cells," J. Biol. Chem., 263:5624-5633 (1988).
Sasaki et al., "Retinal drug delivery using eyedrop preparations of poly-L-lysine-modified liposomes," Eur J Pharm Biopharm, 2013; 83(3):364-9.
Satici et al., "Malondialdehyde and antioxidant enzyme levels in the aqueous humor of rabbits in endotoxin-induced uveitis," Eur J Ophthalmol, 2003; 13(9-10):779-83.
Sayed et al., "Metabolic Activation of R,S-1-(Tetrahydro-2-turanyl)-5-fluorouracil (Ftorafur) to 5-fluorouracil by Soluble Enzymes," Cancer Research, 43:4039-4044 (1983).
Schaumberg et al., "Prevalence of dry eye syndrome among US women," Am J Ophthalmol. 2003;136(2):318-26.
Schaumberg et al., "Epidemiology of dry eye syndrome," Lacrimal Gland, Tear Film, and Dry Eye Syndromes 3, Kluwer Academic/Plenum Publishers, pp. 989-998 (2002).
Schaumberg et al., "Prevalence of Dry Eye Disease among US Men: Estimates from the Physicians' Health Studies," Arch Ophthalmol, 2009; 127(6):763-768.
Schioth et al., "Characterization of the binding of MSH-B, HB-228, GHRP-6 and 153N-6 to the human melanocortin receptor subtypes," Neuropeptides, 31:565-571 (1997).
Schramm et al., "The Cross-linked Biopolymer Hyaluronic Acid as an Artificial Vitreous Substitute," Invest Ophthalmol Vis Sci, 53(2):613-621 (Feb. 2012).
Schwartz and Work, "Measurement and estimation of GFR in children and adolescents," Clin J Am Soc Nephrol. 2009;4(11):1832-43.
Schwartz et al., "Tamponade in surgery for retinal detachment associated with proliferative vitreoretinopathy," Cochrane Database Syst Rev. 2020;5(5):CD006126.
Schwinn et al., "Molecular cloning and expression of the cDNA for a novel alpha 1-adrenergic receptor subtype," J. Biol. Chem., 265:8183-8189 (1990).
Sciuto et al., "Therapeutic Treatments of Phosgene-Induced Lung Injury," Inhal Toxicol, 16(8):565-580 (2004).
Search Report and Written Opinion issued by the Intellectual Property Office of Singapore for Singapore Patent Application No. 11201504859Y dated Aug. 1, 2016 (12 pages).
Serbecic et al., "Anti-oxidative vitamins prevent lipid-peroxidation and apoptosis in corneal endothelial cells," Cell Tissue Res, 320(3):465-75 (Jun. 2005).
Shank et al., "Ion and temperature effects on the binding of gamma-aminobutyrate to its receptors and the high-affinity transport system," J. Neurochem., 54:2007-2015 (1990).
Shen et al., "Molecular cloning and expression of a 5-hydroxytryptamine7 serotonin receptor subtype," J. Biol. Chem., 268:18200-18204 (1993).
Sheppard et al., "Targeting Anterior Uveitis: A Focus on Iontophoresis . . . ", Sep. 1, 2018, Retrieved from Internet URL: https://www.nyee.edu/files/NYEE/Health%20Professionals/Continuing%20Medical%20Education/Enduring%20CME%20Activities/158_supplement.small_v1_FINAL%20082818.pdf.
Sheppard et al., "A Randomized, Comparator-Controlled Phase 2 Clinical Trial of ADX-102 Ophthalmic Solution in Noninfectious Anterior Uveitis," ARVO Annual Meeting Abstract, Invest Ophth Vis Sci. 2017; 58(8):1231.
Sherman et al., "Cellular Defenses Against Unfolded Proteins: A Cell Biologist Thinks about Neurodegenerative Diseases," Neuron, 29(1):15-32 (2001).
Shipp et al., "Common acute lymphoblastic leukemia antigen (CALLA) is active neutral endopeptidase 24.11 ("enkephalinase"): direct evidence by cDNA transfection analysis," Proc Natl Acad Sci USA. 86:297 (1989).
Shoemaker et al., "[3H]diltiazem binding to calcium channel antagonists recognition sites in rat cerebral cortex," Eur. J. Pharmacol., 111:273-277 (1985).
Siegrist et al., "Radioreceptor assay for alpha-MSH using mouse B16 melanoma cells+.," J. Recep. Res., 8:323-343 (1988).
Sieving et al., "Inhibition of the Visual Cycle in vivo by 13-cis Retinoic Acid Protects from Light Damage and Provides a Mechanism for Night Blindness in Isotretinoin Therapy," Proc Natl Acad Sci USA, 98(4):1835-1840 (2001).
Sills et al., "[3H]CGP 39653: a new N-methyl-D-aspartate antagonist radioligand with low nanomolar affinity in rat brain," Eur. J. Pharmacol., 192:19-24 (1991).
Simeone et al., "Modification of the Pyridine Moiety of Nonpeptidyl Indole GnRH Receptor Antagonists," Bioorganic & Medicinal Chemistry Letters, 12(22):3329-3332 (2002).
Simonin et al., "The human delta-opioid receptor: genomic organization, cDNA cloning, functional expression, and distribution in human brain," Mol. Pharmacol., 46:1015-1021 (1994).
Singh et al., "The epidemiology of ocular and nasal allergy in the United States, 1988-1994," J. Allergy Clin. Immunol., 2010; 126(4):778-783.
Smit et al., "Regulation of the human histamine H1 receptor stably expressed in Chinese hamster ovary cells," Brit. J. Pharmacol., 117:1071-1080 (1996).
Smith and Cass, "Oxidative stress and dopamine depletion in an intrastriatal 6-hydroxydopamine model of Parkinson's disease," Neuroscience. 2007;144(3):1057-66.
Smith et al., "Basic pathogenic mechanisms operating in experimental models of acute anterior uveitis," Immunol Cell Biol, 1998; 76:497-512.
Snead et al., "Gamma-hydroxybutyric acid," New England Journal of Medicine, 352(26):2721-2732 (2005).
Snell et al., "Novel structure having antagonist actions at both the glycine site of the N-Methyl-D-Aspartate receptor and neuronal

(56) References Cited

OTHER PUBLICATIONS voltage-sensitive sodium channels. Biochemical, electrophysiological, and behavioral characterization," J Pharmacol Exp Ther, 292(1):215-227 (2000).
Spadea et al., "Corneal wound healing after laser vision correction," Br J Ophthalmol. 2016; 100:28-33.
Spagnol et al., "Efficient synthesis of tricyclic benzobisoxazines by silica gel catalysis," J Org Chem, 2;72(5):1867-1869 (Mar. 2007).
Sparrow et al. "Phospholipid meets all-trans-retinal: the making of RPE bisretmoids," Journal of Lipid Research, 51: 247-261 (2010).
Speth et al., "Benzodiazepine receptors: temperature dependence of [3H]flunitrazepam binding," Life Sci., 24:351-358 (1979).
Stefánsson and Loftsson, "Cyclodextrins in Eye Drop Formulations," J Incl Phenom Macrocycl Chem. 2002;44:23-27(abstract).
Stehle et al., "Molecular cloning and expression of the cDNA for a novel A2-adenosine receptor subtype," Mol. Endocrinol., 6:384-393 (1992).
Stevenson et al., "Dry eye disease: an immune-mediated ocular surface disorder," Arch Ophthalmol. 2012; 130(1): 90-100.
Struys et al., "Determination of the GABA analogue succinic semialdehyde in urine and cerebrospinal fluid by dinitrophenylhydrazine derivatization and liquid chromatography-tandem mass spectrometry: application to SSADH deficiency," J Inherit Metab Dis., 28(6):913-20 (2005).
Struys et al., "Metabolism of gamma-hydroxybutyrate to d-2-hydroxyglutarate in mammals: further evidence ford-2-hydroxyglutarate transhydrogenase," Metabolism, 55(3):353-8 (2006).
Study showing effect of ADX-102 on Fibrotic Changes in Cardiac Fibroblasts Following Cell Stress, American Society for Cell Biology Annual Meeting, Dec. 3-7, 2016 (2 pages).
Sus et al., "Uber die Lichtreaktion der o-Chinondiazide V Mitteilungl) Ubergange heterocyclischer 6-Ringe in heterocyclische 5-Ringe," Liebigs Ann. Chem. 583:150 (1953).
Tahara et al., "Pharmacological characterization of the human vasopressin receptor subtypes stably expressed in Chinese hamster ovary cells," Brit. J. Pharmacol., 125:1463-1470 (1998).
Tang-Liu et al., "Effects of four penetration enhancers on corneal permeability of drugs in vitro," Journal of Pharmaceutical Sciences, 1994; 83(1):85-90.
Tatsumi et al., "Pharmacological profile of neuroleptics at human monoamine transporters," Eur. J. Pharmacol., 368: 277-283 (1999).
Tayeh et al., "Macrophage oxidation of L-arginine to nitric oxide, nitrite, and nitrate. Tetrahydrobiopterin is required as a cofactor," J. Biol. Chem., 264:19654-19658 (1989).
Tempest-Roe et al., "Local therapies for inflammatory eye disease in translation: past, present and future," BMC Ophthalmol., 2013; 13(1):39.
Tewari-Singh et al., "Silibinin attenuates sulfur mustard analog-induced skin injury by targeting multiple pathways connecting oxidative stress and inflammation," PLoS One 7(9):e46149 (2012).
Tian et al., "First total synthesis and determination of the absolute configuration of 1-N-methyl-3-methylamino- [N-butanoicacid-3-(9-methyl-8-propen-7-one)-amide]—benzo [f][1,7]naphthyridine-2-one, a novel benzonaphthyridine alkaloid," Tetrahedron Letters, 53:4892-4895 (2012).
Tikly et al., "Lipid peroxidation and trace elements in systemic sclerosis," Clinical Rheumatology, 25(3):320-324 (2006).
Torkildsen et al., "Efficacy and safety of olopatadine hydrochloride 0.77% in patients with allergic conjunctivitis using a conjunctival allergen-challenge model," Clinical Ophthalmology, 9:1703-1713 (2015).
Toth et al., "A simple, continuous fluorometric assay for HIV protease," Int. J. Pept. Protein Res., 36:544-550 (1990).
Tsugeno et al., "Regions of the molecule responsible for substrate specificity of monoamine oxidase A and B: a chimeric enzyme analysis," J. Biochem., 118 (5) 974-80 (1995).
Tsuzuki et al., "Molecular cloning and expression of the gene encoding human angiotensin II type 2 receptor.," Biochem. Biophys. Res. Commun., 200:1449-1454 (1994).
Tukozkan et al., "Measurement of Total Malondialdehyde in Plasma and tissues by High-Performance Liquid Chromatography and Thiobarbituric Acid Assay," Firat Tip Dergisi, 11 (2):88-92 (2006).
Turk et al., "Serum anti-carbonic anhydrase antibodies and oxidant-antioxidant balance in patients with acute anterior uveitis," Ocul Immunol Inflamm, 22(2):127-32 (Apr. 2014).
Ueda et al., "Evaluation of a Sulfobutyl Ether 13-Cyclodextrin as a Solubilizing/Stabilizing Agent for Several Drugs," Drug Dev Ind Pharm, 24(9):863-867(1998).
Upadhyaya et al., "The sphingolipid degradation product trans-2-hexadecenal forms adducts with DNA," Biochem Biophy Res Comm., 424(1):18-21 (2012).
Vanachayangkul et al., "Inhibition of heme peroxidases by melamine," Enzyme Research, 2012:416062 (2012).
Vignon et al., "[3H]thienyl-phencyclidine ([3H]TCP) binds to two different sites in rat brain. Localization by autoradiographic and biochemical techniques," Brain Res., 378:133-141 (1986).
Vlaskina et al., "Novel Synthesis of Substituted Benzimidazoles by Reduction of Esters of 4-Alkylamino-3,5-dinitrobenzoic Acids by Tin Chloride," Chemistry of Heterocyclic Compounds, vol. 40(4):523-524 (2004).
Vogel et al., "Thirty years beyond discovery-clinical trials in succinic semialdehyde dehydrogenase deficiency, a disorder of GABA metabolism," J Inherit Metab Dis., 36(3):401-10 (2013).
Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 277(5):3397-3403 (2002).
Wagner et al., "Omega-conotoxin GVIA binding to a high-affinity receptor in brain: characterization, calcium sensitivity, and solubilization," J. Neurosci., 8:3354-3359 (1988).
Wakamatsu et al., "Evaluation of lipid oxidative stress status and inflammation in atopic ocular surface disease," Mol Vis, 16:2465-75 (Nov. 2010).
Wall et al., "Plant Antitumor Agents. 30. Synthesis and Structure Activity of Novel Camptothecin Analogs," J. Med. Chem., 36(18):2689-2700 (1993).
Walter et al., "Novel Complex N-Heterocycles via Intramolecular 1,5-Electrocyclizations: 1,2,3,4,4a,5,5a, 10-Octahydropyrido-[4",3":2',3']cyclobuta[1',2':4,5]pyrrolo[2,3-b]pyridines," Heterocycles, 48(8):1581-1591 (1998).
Wang et al., "A facile one-pot synthesis of 2-substituted-3-aminoquinolines: Preparation of benzo[b]naphthyridine-3-carbonitriles," Tetrahedron, 60(13):2937-2942 (2004).
Wang et al., "Human mu opiate receptor. cDNA and genomic clones, pharmacologic characterization and chromosomal assignment," FEBS Lett., 338:217-222 (1994).
Wang et al., "Markers of oxidative and nitrosative stress in systemic lupus erythematosus: correlation with disease activity," Arthritis and Rheumatism, 62(7):2064-2072 (2010).
Wang, X.K., "Pharmacological study on recombinant human GABA-A receptor complex containing alphas (leucine 155 to valine) combined with beta3gamma2s subunits," Acta. Pharmacol. Sin., 22:521-523 (2001).
Waslidge et al., "A colorimetric method for the determination of lipoxygenase activity suitable for use in a high throughput assay format," Anal. Biochem., 231:354-358 (1995).
Weaver et al., "The Th17 pathway and inflammatory diseases of the intestines, lungs, and skin," Annu. Rev. Pathol., 8:477-512 (2013).
Webb et al., "Intralesional cytokines in chronic oxazolone-induced contact sensitivity suggest roles for tumor necrosis factor alpha and interleukin-4," J Invest Dermatol, 111(1):86-92 (Jul. 1998).
Weishaar et al., "Multiple molecular forms of cyclic nucleotide phosphodiesterase in cardiac and smooth muscle and in platelets. Isolation, characterization, and effects of various reference phosphodiesterase inhibitors and cardiotonic agents," Biochem. Pharmacol., 35:787-800 (1986).
Weng et al., "Insights into the Function of Rim Protein in Photoreceptors and Etiology of Stargardt's Disease from the Phenotype in abcr Knockout Mice," Cell, 98(1):13-23 (1999).
Westphal et al., "Reactions with Pryridinium Pyruvic Acid Esters," Pharmazie, 31(11)770-773 (1976) [English Translation].

(56) References Cited

OTHER PUBLICATIONS

Wieland et al., "Subtype selectivity and antagonistic profile of the nonpeptide Y1 receptor antagonist BIBP 3226," J. Pharmacol. Exp. Ther., 275:143-149 (1995).

Winfield and Richards, "Ophthalmic products," Pharmaceutical Practice, Churchill Livingstone. 2004;265-268.

Witt-Enderby et al., "Characterization and regulation of the human ML1A melatonin receptor stably expressed in Chinese hamster ovary cells," Mol. Pharmacol., 50:166-174 (1996).

Wolkenberg et al., "Design, synthesis, and evaluation of novel 3,6-diaryl-4-aminoalkoxyquinolines as selective agonists of somatostatin receptor subtype 2," J Med Chem, 54(7):2351-2358 (2011).

Wood et al., "Aldehyde Load in Ischemia-Reperfusion Brain Injury: Neuroprotection by Neutralization of reactive Aldehydes with Phenelzine," Brain Res, 1122(1):184-190 (2006).

Wood et al., "The concept of "aldehyde load" in neurodegenerative mechanisms: cytotoxicity of the polyamine degradation products hydrogen peroxide, acrolein, 3-aminopropanal, 3-acetamidiorioanal and 4-aminobutanal in a retinal ganglion cell line," Brain Research, 1145:150-156 (2007).

Wurch et al., "Sequence and functional analysis of cloned guinea pig and rat serotonin 5-HT1D receptors: common pharmacological features within the 5-HT1D receptor subfamily," J. Neurochem., 68:410-418 (1997).

Wynn, "Cellular and molecular mechanisms of fibrosis," J Pathol. 2008;214(2):199-210.

Yadav et al., "Regulation of NF-kB-Induced Inflammatory Signaling by Lipid Peroxidation-Derived Aldehydes," Oxidative Med & Cell Longev, 2013, Art ID 690545, 11 pages (2013).

Yarnell, "Light Flips the Lipid Switch: Palmitoylation—the reversible attachment of palmitate to proteins—gets a new role in vision," C&EN, 82(29):22-23 (2004).

Yokomizo et al., "Hydroxyeicosanoids bind to and activate the low affinity leukotriene B4 receptor, BLT2," J. Biol. Chem., 276:12454-12459 (2001).

Yu et al., "Injectable Chemically Crosslinked Hydrogel for the Controlled Release of Bevacizumab in Vitreous: A 6-Month In Vivo Study," Transl Vis Sci Technol, 4(2,5):1-11 (2015).

Zagol-Ikapitte et al., "Characterization of scavengers of γ-ketoaldehydes that do not inhibit prostaglandin biosynthesis," Chem Res Toxicol, 23(1):240-250 (2010).

Zarkovic "4-hydroxynonenal and neurodegenerative diseases," Molecular Aspects of Medicine, 2003; 24(4-5):293-303.

Zava et al., "Androgen receptor assay with [3H]methyltrienolone (R1881) in the presence of progesterone receptors," Endocrinology, 104:1007-1012 (1979).

Zhang et al., "Potent nonsteroidal progesterone receptor agonists: synthesis and SAR study of 6-aryl benzoxazines," Bioorg Med Chem Lett, 12(5):787-90 (Mar. 2002).

Zhang et al., "Practical ophthalmic pharmacology," People's Military Medical Press, 2015; p. 590.

Zhou et al., "Chemical and biological evidence for base propenals as the major source of the endogenous M1dG adduct in cellular DNA," J Biol Chem., 280(27):25377-82 (2005).

Zhou et al., "Cloning and expression of human and rat D1 dopamine receptors," Nature, 347:76-80 (1990).

Zhou et al., "Mechanisms for the induction of HNE- MDA- and AGE-adducts, RAGE and VEGF in retinal pigment epithelial cells," Exp Eye Res., 80(4):567-80 (2005).

Office Action for Canadian Patent Application No. 2,782,015 mailed Apr. 5, 2017.

Office Action for Canadian Patent Application No. 2,782,015 mailed Feb. 14, 2018.

Office Action for Canadian Patent Application No. 2,782,015 mailed Oct. 9, 2018.

Office Action for Canadian Patent Application No. 2,782,015 mailed Jun. 13, 2019.

U.S. Appl. No. 18/236,795 of Brady et al., filed Aug. 22, 2023.

U.S. Appl. No. 18/568,566 of Brockman et al., filed Dec. 8, 2023.

COMPOSITIONS AND METHODS FOR THE TREATMENT OF MACULAR DEGENERATION

RELATED APPLICATION

This application is a continuation of U.S. patent application Ser. No. 15/782,470, filed on Oct. 12, 2017, which is a continuation of U.S. patent application Ser. No. 13/514,769, filed on Aug. 17, 2012, now U.S. Pat. No. 9,814,701, which is a U.S. national phase application of PCT/US2010/059719, filed on Dec. 9, 2010, which claims the benefit of U.S. Provisional Application No. 61/285,745, filed on Dec. 11, 2009. The entire contents of these applications are incorporated herein by reference in their entireties.

BACKGROUND OF THE INVENTION

Macular degeneration is a leading cause of progressive blindness. The macula is the central region of the retina and contains the fovea where high acuity central vision is processed. Macular degeneration is a neurodegenerative disease in the macula that progressively causes disabling deficits in visual function.

There are multiple forms of macular degeneration. Age-related macular degeneration (AMD) is the most common form and first appears at middle age or later. In AMD patients, the dry form normally occurs first and develops with no vascular complications. Its clinical signs include an increase in fundus auto-fluorescence (FAF) and the formation of extracellular deposits called soft drusen, both caused by the accumulation of lipofuscin in retinal pigment epithelial (RPE) cells as discussed below. About 40% of dry AMD patients progress to an advanced form of the disease called geographic atrophy (GA) secondary to dry AMD, which is characterized by one or more atrophic retinal lesions caused by the localized death of RPE cells and adjacent retinal photoreceptor cells. Another 10% of dry AMD patients progress to wet AMD, which is characterized by neovascular growth from the choroid into the retina in response to VEGF signaling by RPE cells that are undergoing severe oxidative stress from A2E toxicities. Choroidal neovascular growth disrupts retinal tissue and destroys visual function in regions of the macula where this occurs. Finally, there is an early onset form of macular degeneration called Stargardt's disease which first appears in teenagers and young adults. Stargardt's disease is believed to have the same etiology as dry AMD.

Multiple lines of evidence indicate that macular degeneration is caused by the cytotoxic accumulation in RPE cells of naturally occurring bis-retinoid compounds including A2E (Sparrow J R, Wu Y, Kim C Y, Zhou J. Phospholipid meets all-trans-retinal: the making of RPE bisretinoids. J Lipid Res. 2009 Aug. 7 e-published). A2E is a reaction product of all-trans retinaldehyde (RAL) and phosphatidylethanolamine (PE), a membrane phospholipid found in the disc membranes of photoreceptor outer segments. The RAL that reacts with PE escapes from the visual cycle (step 3b in FIG. 1), a metabolic pathway in the back of the eye that (i) converts vitamin A from an alcohol (retinol) to a photo-reactive aldehyde (11-cis-retinaldehyde) for use in photo-transduction by opsin proteins in photoreceptor cell outer segments, and (ii) converts RAL to retinol after photo-transduction. As RAL escapes the visual cycle, A2E precursors form reversibly in photoreceptor outer segments, which are ingested by neighboring RPE cells after diurnal shedding. The final and irreversible step in the biosynthesis of A2E takes place in the acidic environment of RPE cell lysosomes. As A2E accumulates in RPE cells, it gradually poisons them by multiple cytotoxic mechanisms including lysosomal failure. This leads to the accumulation of undigested cellular debris called lipofuscin, which contains A2E and can be detected clinically by FAF. As RPE cells deteriorate, they lose their ability to participate in the visual cycle and are unable to provide photoreceptors with other metabolic support required for normal retinal function (see FIG. 1; Lamb T D, Pugh E N, Dark adaptation and the retinoid cycle of vision. Prog. Retinal and Eye Res. 2004; 23:307). As their metabolic support is withdrawn, photoreceptors fail to renew their shed outer segments and visual function is progressively lost. Reducing A2E formation will allow RPE cells to recover from A2E poisoning and resume their normal metabolic support of photoreceptor cells.

WO 2006/127945 discloses compounds and compositions that have been shown to reduce the formation of A2E, which as described above is the underlying etiology of macular degeneration including dry AMD and Stargardt's disease. These compounds are designed to inhibit A2E biosynthesis by reducing the amount of free RAL available for reaction with PE in photoreceptor outer segments, which is the first step in the A2E biosynthetic pathway. These compounds are lipophilic by design (i.e. the logarithm of their measured or calculated partition constant between water and n-octanol [log P or clogP which are called log D or clogD respectively at pH 7.4 as used herein] is greater than 0), because their covalent reactions with RAL take place in the disc membranes of photoreceptor outer segments where A2E precursors form.

A different way to reduce A2E biosynthesis is to inhibit one or more proteins of the visual cycle, because when the visual cycle is inhibited, less RAL escapes the visual cycle and becomes available to react with PE and form A2E precursors. Chronic treatment with a visual cycle inhibitor has been shown to reduce A2E synthesis in mouse (Radu et al., Treatment with isotretinoin inhibits lipofuscin accumulation in a mouse model of recessive Stargardt's macular degeneration. Proc Natl Acad Sci USA. 2003;100:4742). The clinical value of this treatment approach is limited by the fact that visual cycle inhibitors cause night blindness by lowering rod photoreceptor sensitivity, impair dark adaptation by slowing the dark adaptation rate, and cause retinoid toxicities by activating retinoic acid receptors (RAR) if the visual cycle inhibitor compound is a member of the retinoid class. Visual cycle inhibitors now in clinical development include fenretinide which is a retinoid compound, and ACU-4429 which reportedly is not a retinoid.

Other approaches to treating macular degeneration are based on neuroprotection mechanisms of action including but not limited to neurotrophic receptor agonists, anti-inflammatory compounds including complement cascade inhibitors, anti-apoptosis compounds, steroids and anti-oxidant compounds, and limiting the progression to wet AMD with VEGF receptor blockers which mitigate the effects of VEGF signaling by RPE cells that are in severe oxidative stress as a consequence of A2E toxicities.

SUMMARY OF THE INVENTION

In therapeutic and prophylactic use, topical ocular administration minimizes systemic exposure compared to oral dosing. The present invention provides formulations and methods for topical ocular dosing of lipophilic compounds which treat macular degeneration (including dry AMD, GA secondary to dry AMD, wet AMD and Stargardt's disease)

by reducing the formation of A2E and other naturally occurring bis-retinoids, by reacting covalently with free RAL that escapes the visual cycle and would otherwise form precursors of these compounds. The lipophilic compounds within the scope of this invention are further defined by having a log P or clogP (log D or clogD at pH=7.4) greater than 0.

DETAILED DESCRIPTION OF THE INVENTION

Figure 1:
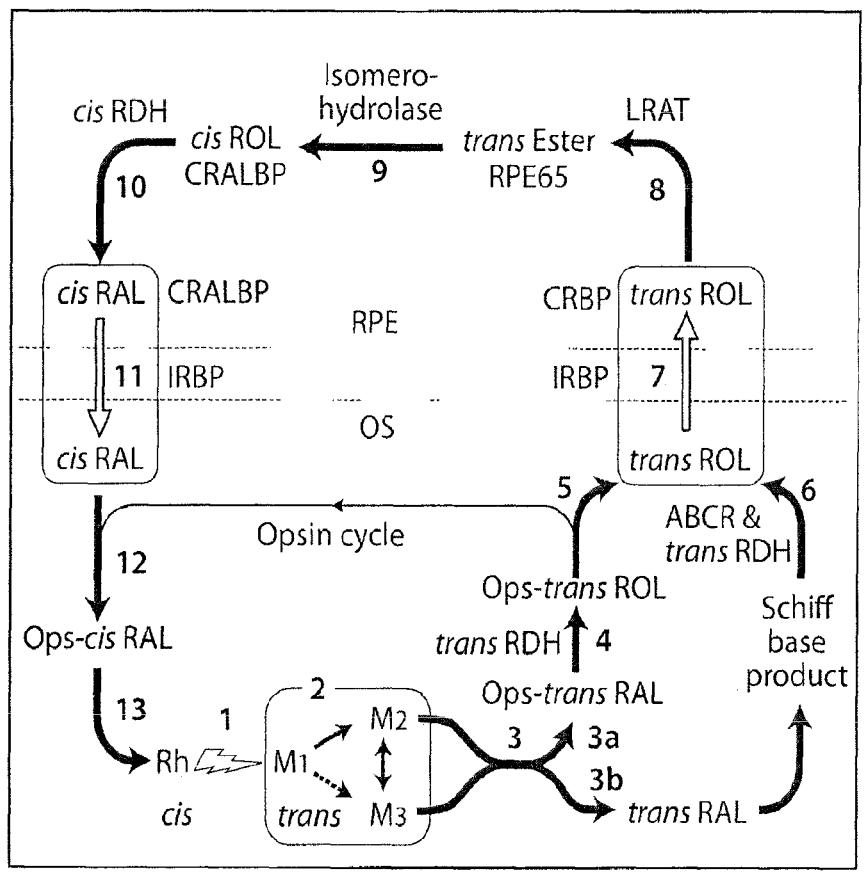
FIG. 1 depicts the visual cycle.

One embodiment of the present invention provides pharmaceutical compositions for treating macular degeneration (including dry AMD, GA secondary to dry AMD, wet AMD and Stargardt's disease). The root cause of macular degeneration is the cytotoxic accumulation in RPE cells of naturally occurring bis-retinoids including A2E. This accumulation can be lowered pharmacologically by limiting the amount of free RAL that escapes the visual cycle and otherwise reacts with PE to form their precursors. As the accumulation of these compounds is reduced pharmacologically, RPE cells can recover from cytotoxic damage and resume their metabolic support of photoreceptors which is essential for normal visual function. In publication WO 2006/127945, compounds are described which reduce A2E accumulation in this manner and are therefore useful in treating macular degeneration. The instant application incorporates by reference the subject matter of WO 2006/127945.

Lipophilic compounds which reduce A2E and thereby treat macular degeneration including dry AMD and Stargardt's disease by other means (e.g. by inhibiting the visual cycle) are also included within the scope of this invention. Such compounds include ACU-4429. All such compounds have a log P or clogP greater than 0.

In therapeutic or prophylactic use, topical ocular administration minimizes systemic exposure compared to oral dosing. However, most topical formulations have failed to deliver efficacious levels of drug to the retina which is the site of the mechanism of action. Surprisingly, applicants have found that by employing preparations containing a lipophilic active agent and a cyclodextrin, or chemically modified cyclodextrin including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium salt (or potassium salt), efficacious levels of the lipophilic active agent are delivered to the back of the eye and specifically to the RPE and retina. Pharmaceutical compositions of a lipophilic active agent and an oligomeric or a polymeric carrier such as a cyclodextrin or chemically modified cyclodextrin including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium salt (or potassium salt) are useful for the treatment of macular degeneration (including dry age-related macular degeneration, GA secondary to dry AMD, wet AMD and Stargardt's disease).

One exemplification of the present invention is represented by a topical ophthalmic composition containing an active lipophilic compound and an oligomeric or a polymeric carrier such as a cyclodextrin, or a chemically modified cyclodextrin including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium salt (or potassium salt) in an aqueous solution or a gel dispersion. Such active lipophilic compounds include those that reduce A2E by reacting covalently with RAL, e.g. the compounds of WO 2006/127945. Illustrative of such compounds are those described in WO 2006/127945 the contents of which application are herein incorporated by reference. Exemplifying the compounds which may be employed in the instant invention are the compounds of formula Ia:

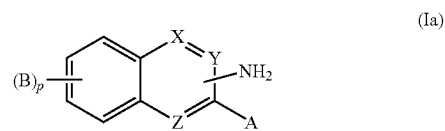

(Ia)

and pharmaceutically acceptable salts thereof, wherein X, Y, and Z are each, independently. N, CH, C with the NH$_2$ attached, or absent, such that one of X, Y, and Z is N; p is 0, 1, 2, or 3, B is a halogen atom, hydroxyl, carbamoyl, amino, or aryl, A is

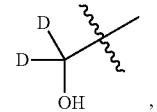

D is unbranched lower alkyl. Specifically, compound A of paragraph (00027) of WO 2006/127945 and pharmaceutically acceptable salts thereof may be employed in the instant invention.

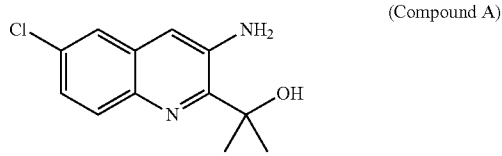 [SMILES: CC(C)(O)c1nc2ccc(Cl)cc2cc1N]

(Compound A)

Further illustrating the useful compounds herein are the compounds of formula IIIa:

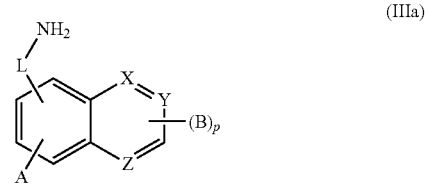

(IIIa)

and pharmaceutically acceptable salts thereof, wherein L is a single bond or CH$_2$; X, Y, and Z are each, independently, N, NH, O, S, CB, CH, or absent, such that one of X, Y, and Z is N or NH; p is 0, 1, 2, or 3; B is a halogen atom, hydroxyl, carbamoyl, aryl or amino; A is

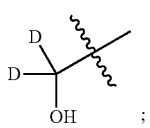

and D is unbranched lower alkyl; and

Specifically, compounds B and C of paragraph (00046) of WO 2006/127945, and pharmaceutically acceptable salts thereof may be employed in the instant invention.

(Compound B)

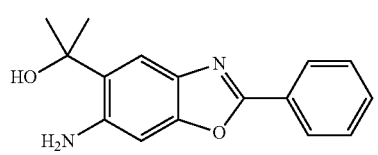

(Compound C)

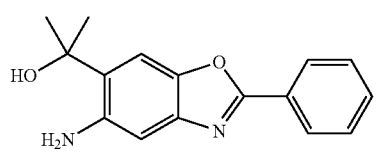

The amount of active agent in the composition will vary dependent on the intrinsic activity of the compound. However, for compounds of formula Ia and formula Ma the amount will generally be from 0.01-1.0% weight/volume and more particularly 0.1% to 0.5% weight/volume. In each case a compound as described above may be used or a pharmaceutically acceptable salt of said compound. The term lipophilic compound is meant to include the compound and its pharmaceutically acceptable salts. A pharmaceutically acceptable salt herein means a salt that is capable of being topically delivered to the eye of a patient. The carrier in the composition is an oligomeric or a polymeric carrier such as a cyclodextrin including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium salt (or potassium salt). Exemplifying an oligomeric or a polymeric carrier is β-cyclodextrin sulfobutylether sodium salt. The amount of β-cyclodextrin sulfobutylether sodium salt in the aqueous preparation may range from about 0.01% to 30% weight/volume. In one illustration the concentration of β-cyclodextrin sulfobutylether sodium salt is 5-25% weight/volume. Further illustrating the concentration of β-cyclodextrin sulfobutylether sodium salt is 9.5-20% weight/volume. In one exemplification the concentration of β-cyclodextrin sulfobutylether is 9.5% weight/volume.

It should be noted that, although the compositions are further illustrated with β-cyclodextrin sulfobutylether, each lipophilic agent may be formulated with each of the excipients. The composition may contain saline and be buffered with for example a phosphate buffer so that the pH of the composition is brought to a pH range of 5.5-8.5 or more particularly a pH of 6.5-7.5. A preservative may optionally be included in the composition. Such preservatives can include both chemical stabilizers and antiseptics. Compounds such as Compounds A are stable under the conditions of use, however other compounds may require the use of other excipients such as anti-oxidants.

A second embodiment of the invention is directed to a method of treating macular degeneration (including dry age-related macular degeneration, GA secondary to dry AMD, wet AMD and Stargardt's disease), by administering a topical formulation of an active lipophilic compound and a carrier to the eye(s) of a patient. In another embodiment, the present invention provides a topical ophthalmic composition for use in treating macular degeneration wherein said composition comprises an active lipophilic compound and a carrier or a pharmaceutically acceptable salt thereof in an aqueous solution. Exemplifying the carrier is β-cyclodextrin sulfobutylether or a pharmaceutically acceptable sat thereof. The active lipophilic compound in each of these embodiments includes those that reduce A2E by reacting with RAL, e.g. the compounds of WO 2006/127945. Examples of such compounds are those described in WO 2006/127945. Exemplifying such compounds are Compounds A, B and C. Lipophilic Compounds which function by other mechanisms such as ACU-4429 are also included. The term lipophilic compound is meant to include both the compound and its pharmaceutically acceptable salts. The excipient in the formulation is oligomeric or polymeric such as a cyclodextrin or a chemically modified cyclodextrin, more particularly including β-cyclodextrin sulfobutylether sodium salt (or potassium salt). It should be noted that, although particularly illustrated with β-cyclodextrin sulfobutylether, the method may be practiced with each lipophilic compound formulated with each excipient. The formulation may be buffered to a pH range of 5.5-8.5 or more particularly a pH of 6.5-7.5. The buffer may be a phosphate buffer. The formulation may be applied as an aqueous solution or a gel dispersion and the solution may be a saline solution. The accumulation of lipofuscin occurs in RPE cells in the back of the eye. Applicants have determined experimentally in animals that the use of topical compositions as described herein deliver pharmacologically active levels of lipophilic active drug safely to the back of the eye after topical ocular administration and are therefore useful in the treatment of macular degeneration (including dry age-related macular degeneration, GA secondary to dry AMD, wet AMD and Stargardt's disease). Efficacious levels are defined as those that reduce A2E accumulation significantly in animal studies.

Preparation of Compositions of the Invention

Formulations of a lipophilic active agent and an oligomeric or a polymeric carrier are prepared by stirring an aqueous suspension or solution of a polymeric carrier such as a cyclodextrin, or chemically modified cyclodextrin including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium (or potassium) salt with water, saline or phosphate-buffered saline at a temperature from 20° C. to 50° C., but preferably at ambient temperature, for 0.1-24 hr, depending on the polymeric carrier. The lipophilic active agent is added as a solid or neat liquid to the thus formed aqueous suspension or solution of polymeric carrier, and the resulting mixture is stirred at a temperature from 20° C. to 50° C., but preferably at ambient temperature, for 0.1-24 hr, but typically from 0.5-2 hr, depending on the lipophilic active agent. The thus formed formulation of a lipophilic active agent and an oligomeric or a polymeric carrier may then be treated with an aqueous solution of an inorganic or organic acid or an inorganic or organic base to adjust the pH of the solution as desired. To the formulation may also be added preservatives, including both chemical stabilizers and antiseptics.

Example 1—Preparation of a 0.1% w/v Aqueous Formulation of Compound a with 9.5% w/v β-Cyclodextrin Sulfobutylether The preparation was carried out in a 1000 ml beaker equipped with a stirring bar for mixing. Approximately 60% of the targeted weight of sterile water was added to the beaker. Stirring was adjusted so as not to incorporate air. Anhydrous dibasic sodium phosphate (0.83% of the total batch weight) and sodium phosphate monobasic monohydrate (0.017% of the total batch weight) was added to the vessel and mixed until dissolved. β-cyclodextrin sulfobutylether (9.5% of the total batch weight) was slowly added to the beaker and the solution mixed until dissolved. Compound A (0.1% of the total batch weight) was slowly added and mixed until dissolved. A sample was extracted and the pH measured. If the pH was not in the range 7.3±0.05, adjustment was made with IN aqueous NaOH or IN aqueous HCl. The batch weight was measured and the amount of sterile water needed to bring to final batch weight was determined and added.

Results of Applying Formulations to the Eyes of Mice and Rabbits

1) Measurement of levels of $^{14}$C-Compound A in the posterior eyecup of mice.

The target tissue, for the biological activity of compounds which reversibly react with RAL, e.g. Compounds A, B and C, is the outer segment of retinal photoreceptor cells. To demonstrate that topical optical (TO) administration of Compound A delivers therapeutically useful amounts of, for example, Compound A to the retina, C57BL/6 mice, the parent strain of abcr −/− mice (knockout mouse), were treated intraperitoneally (IP) with $^{14}$C-Compound A at 10 mg/kg ("efficacious dose"), specifically a dose that when repeated daily for 56 days reduced A2E formation by 71% (p<0.01) in the abcr −/− mouse. At certain timepoints after topical ocular dosing, the eyes of the mice were enucleated and the posterior eyecup was dissected, extracted and analyzed by liquid scintillation chromatography (LSC) for $^{14}$C-Compound A. Thirty minutes after IP treatment with $^{14}$C-Compound A, the $C_{max}$ amount of $^{14}$C-Compound A in the posterior eyecup (i.e. the peak concentration at time $T_{max}$) was 14.36 µg/g. Fifteen minutes after TO treatment with a single 5 µL eyedrop containing 25 µg (0.5% weight/volume) $^{14}$C-Compound A in a composition containing 20% weight/volume β-cyclodextrin sulfobutylether sodium salt in phosphate-buffered saline, the equivalent amount of $^{14}$C-Compound A in the posterior eyecup was 13.12 µg/g, which is 90% of the $C_{max}$ value measured in the same ocular tissue after systemic treatment at an efficacious dose.

2) Ocular levels of $^{14}$C-Compound A in the retina and RPE of rabbits.

Dutch belted rabbits were dosed TO with a single 40 µL eyedrop containing either 0.50%, 0.15% or 0.05% weight/volume $^{14}$C-Compound A in 20%, 6% or 2% weight/volume, respectively, β-cyclodextrin sulfobutylether sodium salt in phosphate-buffered saline (Table 1). At different times after dosing the eyes of the rabbits were enucleated, dissected and the amount of $^{14}$C-Compound A in the retina and RPE together was measured by LSC. Each value represents the mean value from 6 eyes. Significant amounts of $^{14}$C-Compound A were found in rabbit retina/RPE within one hour of TO dosing as shown in Table 1.

3) Topical Ocular Dosing with $^{14}$C-Compound A in Cynomolgus Macaques.

Figure 2:
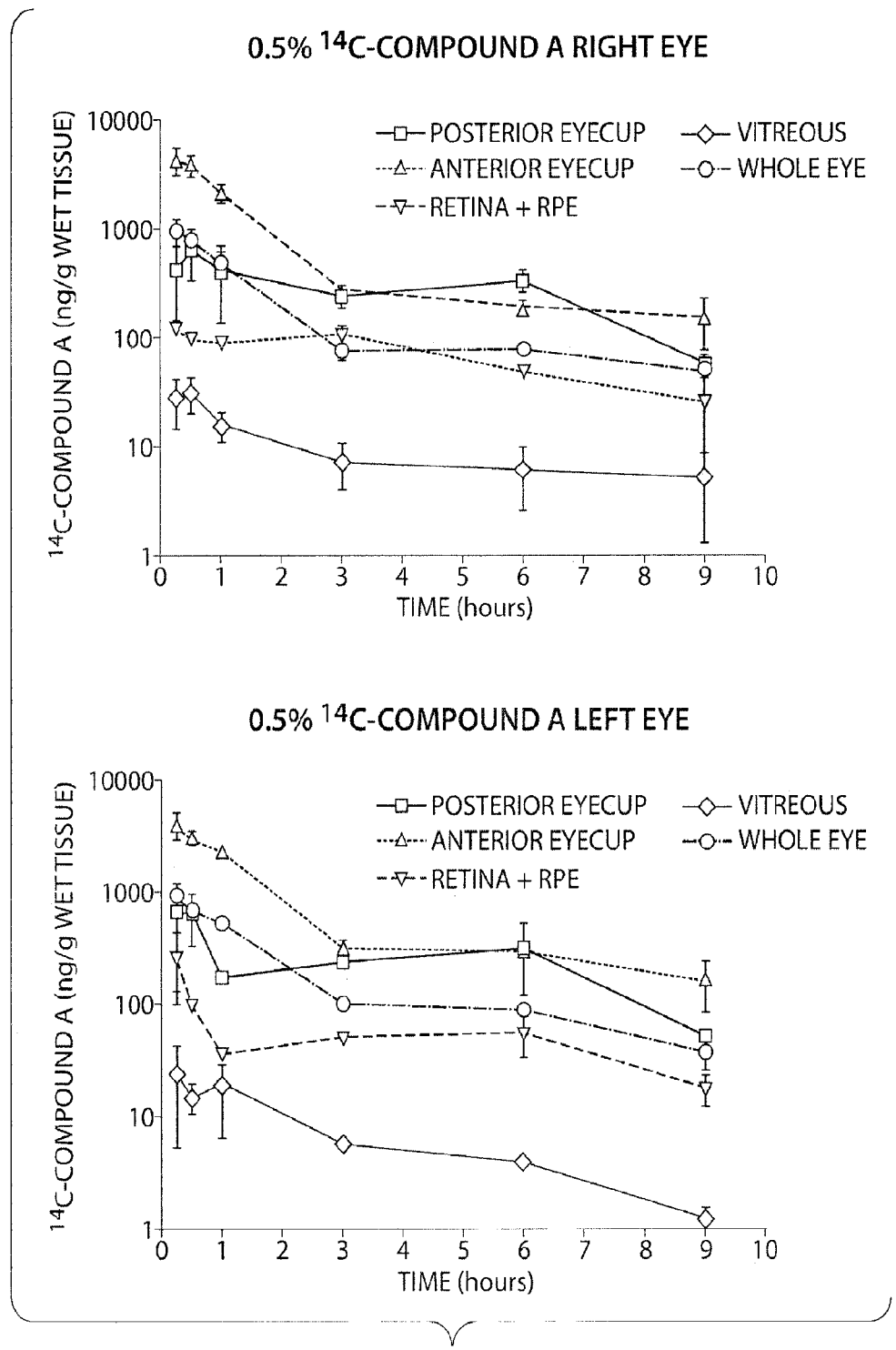
FIG. 2 depicts a time profile of the concentration of $^{14}$C-Compound A in ng/g of ocular tissue.

The pharmacokinetics (PK) of Compound A in four intraocular regions of Cynomolgus Macaques was measured after topical dosing of 40 µL per eye of 0.50% weight/volume $^{14}$C-Compound A in β-cyclodextrin sulfobutylether sodium salt in phosphate-buffered saline. Sampling of intraocular regions (vitreous humor, retina+RPE, anterior eyecup, and posterior eyecup) and blood for PK evaluation was conducted at 0.25, 0.5, 1, 3, 6 and 9 hours post dose. FIG. 2 shows the time course of $^{14}$C-Compound A concentration expressed in nanograms (ng) per gram (g) of ocular tissue.

TABLE 1

$^{14}$C-Compound A levels in rabbit retina and RPE after acute TO dosing in β-cyclodextrin sulfobutylether sodium salt.

| Compound A concentration in eyedrop (% w/v) | Amount applied of $^{14}$C-compound A (ng) | βCSSA[1] (% w/v) | Amount of $^{14}$C-compound A in retina and RPE at $t_{max}$ (ng/g) |
|---|---|---|---|
| 0.50% | 200 | 20% | 131 |
| 0.15% | 60 | 6% | 47.0 |
| 0.05% | 20 | 2% | 23.1 |

[1]β-cyclodextrin sulfobutylether sodium salt; w/v = weight/volume.

4) Functional biological activity in mice.

The biological activity in the retina of some drugs within the scope of the invention such as Compounds A, B and C cannot be measured non-invasively after topical ocular application because these drugs, e.g. Compounds A, B and C, do not alter the normal function of the retina. For example Compound A does not inhibit the visual cycle nor does it slow the rate of dark adaptation (DA), changes which can be measured by electroretinography (ERG) within minutes after equivalent treatment with a visual cycle inhibitor. The protocol for measuring DA rates by ERG is based on the kinetics of functional visual recovery from photo-bleaching of visual pigment by brief exposure to extremely bright light. Like Compounds A, B and C, retinoids are lipophilic compounds as defined above. As such, retinoids can be used to demonstrate that a small lipophilic compound in a composition containing β-cyclodextrin sulfobutylether sodium salt exhibits biological activity in the retina minutes to hours after topical application to the front of the eye.

Figure 3:
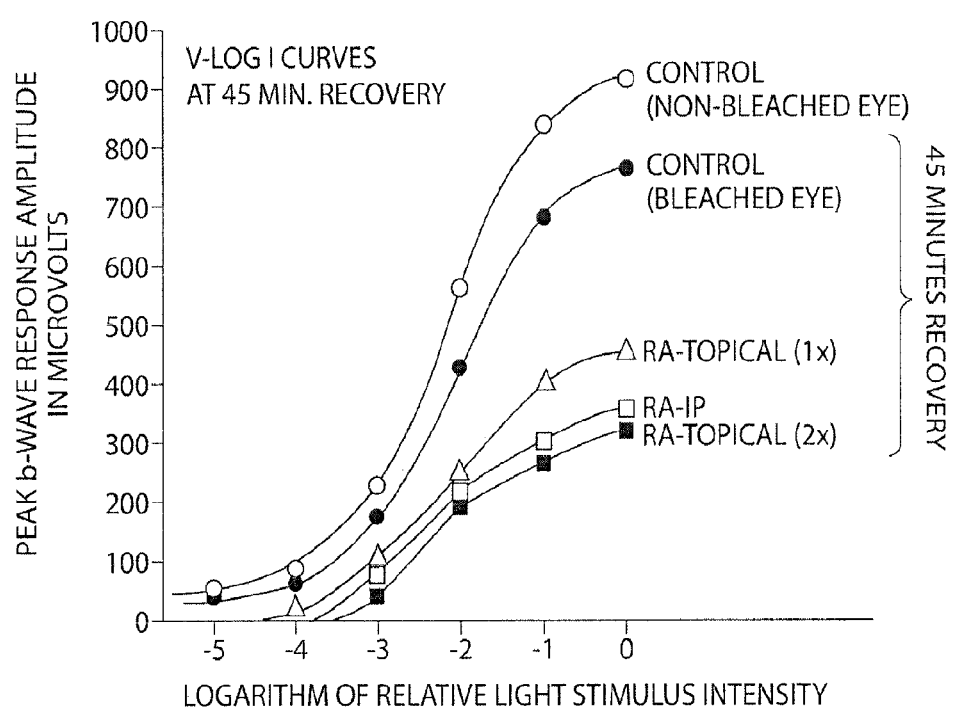
FIG. 3 depicts effects of RA treatment on dark adaptation rate in the mouse after acute TO or IP administration of 13-cis-retinoic acid.

A retinoid useful for this purpose is 13-cis-retinoic acid (RA, also known as isotretinoin). Mice treated IP at 20 mg/kg with RA show visual cycle inhibition (FIG. 3). Independent studies demonstrate that the visual cycle inhibition decreases A2E synthesis (Radu R A, Mata N L, Nusinowitz S, Liu X, Sieving P A, Travis G H. Treatment with isotretinoin inhibits lipofuscin accumulation in a mouse model of recessive Stargardt's macular degeneration. Proc Natl Acad Sci 2003;100:4742). However, mice treated TO with one or two 30 µL eyedrops of a composition containing 0.2% weight/volume RA and 20% weight/volume β-cyclodextrin sulfobutylether sodium salt in phosphate-buffered saline showed a dose-responsive inhibition of DA similar to that observed after IP dosing (FIG. 3).

What is claimed is:

1. An ophthalmic composition, comprising compound A

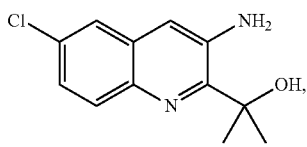
(Compound A)

or a pharmaceutically acceptable salt thereof, and β-cyclodextrin sulfobutylether or a pharmaceutically acceptable salt thereof, in an aqueous solution.

2. The composition of claim 1, wherein the compound is present at 0.1% to 0.5% w/v.

3. The composition of claim 1, wherein the compound is present at 0.5% w/v.

4. The composition of claim 1, wherein the compound is present at 0.15% w/v.

5. The composition of claim 1, wherein the compound is present at 0.05% w/v.

6. The composition of claim 1, wherein the solution is an aqueous saline solution phosphate buffered to a pH of 6.5-7.5.

7. The composition of claim 1, wherein the β-cyclodextrin sulfobutylether is in the form of β-cyclodextrin sulfobutylether sodium salt.

8. The composition of claim 1, wherein the β-cyclodextrin sulfobutylether or pharmaceutically acceptable salt thereof is at a concentration of 0.01-30% w/v.

9. The composition of claim 1, wherein the β-cyclodextrin sulfobutylether or pharmaceutically acceptable salt thereof is at a concentration of 5-25% w/v.

10. The composition of claim 7, wherein the β-cyclodextrin sulfobutylether sodium salt is at a concentration of 5-25% w/v.

11. The composition of claim 1, wherein the β-cyclodextrin sulfobutylether or pharmaceutically acceptable salt thereof is at a concentration of 9.5% w/v.

12. An ophthalmic composition, comprising Compound A

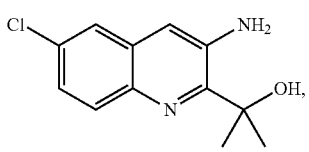
(Compound A)

or a pharmaceutically acceptable salt thereof, and hydroxypropyl β-cyclodextrin or a pharmaceutically acceptable salt thereof, in an aqueous solution.

13. The composition of claim 12, wherein the compound is present at 0.1% to 0.5% w/v.

14. The composition of claim 12, wherein the compound is present at 0.5% w/v.

15. The composition of claim 12, wherein the compound is present at 0.15% w/v.

16. The composition of claim 12, wherein the compound is present at 0.05% w/v.

17. The composition of claim 12, wherein the solution is an aqueous saline solution phosphate buffered to a pH of 6.5-7.5.

18. The composition of claim 12, wherein the hydroxypropyl-β-cyclodextrin is 2-hydroxypropyl-β-cyclodextrin or 3-hydroxypropyl-β-cyclodextrin.

19. The composition of claim 12, wherein the hydroxypropyl-β-cyclodextrin is at a concentration of 5-25% w/v.

* * * * *